US012746203B2

(12) United States Patent
Karve et al.

(10) Patent No.: US 12,746,203 B2
(45) Date of Patent: Sep. 29, 2026

(54) PUMPLESS ENCAPSULATION OF MESSENGER RNA

(71) Applicant: Translate Bio, Inc., Lexington, MA (US)

(72) Inventors: Shrirang Karve, Lexington, MA (US); Priyal Patel, Lexington, MA (US); Natalia Vargas Montoya, Lexington, MA (US); Frank DeRosa, Lexington, MA (US); Michael Heartlein, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 1252 days.

(21) Appl. No.: 17/286,113

(22) PCT Filed: Oct. 18, 2019

(86) PCT No.: PCT/US2019/056936
§ 371 (c)(1),
(2) Date: Apr. 16, 2021

(87) PCT Pub. No.: WO2020/081933
PCT Pub. Date: Apr. 23, 2020

(65) Prior Publication Data

US 2021/0378962 A1 Dec. 9, 2021

Related U.S. Application Data

(60) Provisional application No. 62/747,838, filed on Oct. 19, 2018.

(51) Int. Cl.
*A61K 9/127* (2025.01)
*A61K 9/1271* (2025.01)
(Continued)

(52) U.S. Cl.
CPC .......... *A61K 9/1277* (2013.01); *A61K 9/1271* (2013.01); *A61K 31/7105* (2013.01); *A61K 48/00* (2013.01)

(58) Field of Classification Search
CPC ................ A61K 9/1277; A61K 9/1271; A61K 31/7105; A61K 48/00
See application file for complete search history.

(56) References Cited

U.S. PATENT DOCUMENTS 11,191,849 B2 * 12/2021 Abrams ............... A61K 47/544
11,744,801 B2 * 9/2023 Schariter .................. A61K 9/19
424/450

(Continued)

FOREIGN PATENT DOCUMENTS

CN 103906504 A 7/2014
EP 1203614 5/2002

(Continued)

OTHER PUBLICATIONS

Machine translation of EP1203614A1 from Google Patents, 11 pages. (Year: 2024).*

(Continued)

*Primary Examiner* — Emmanuel S Luk
(74) *Attorney, Agent, or Firm* — LATHROP GPM LLP; James H. Velema, Esq.

(57) ABSTRACT

The present invention provides, among other things, a process of encapsulating messenger RNA (mRNA) in liposomes comprising a. providing a first stream comprising an mRNA solution at a first controlled flow rate, b. providing a second stream comprising a lipid solution at a second controlled flow rate, and c. mixing the first stream and the second stream to form mRNA-encapsulated liposomes, wherein the first controlled flow rate and the second controlled flow rate are achieved without use of a pump.

11 Claims, 10 Drawing Sheets

(51) Int. Cl.

| | |
|---|---|
| ***A61K 9/1277*** | (2025.01) |
| ***A61K 31/7105*** | (2006.01) |
| *A61K 48/00* | (2006.01) |

(56) References Cited

U.S. PATENT DOCUMENTS

| | | | | |
|---|---|---|---|---|
| 12,357,575 | B2 * | 7/2025 | Schariter | A61K 9/19 |
| 2002/0072592 | A1 * | 6/2002 | Ervin, Jr. | A61P 35/04<br>435/7.1 |
| 2004/0032037 | A1 | 2/2004 | Katinger et al. | |
| 2006/0045942 | A1 * | 3/2006 | Sher | B67D 1/0051<br>426/115 |
| 2009/0277833 | A1 * | 11/2009 | Mir | B01D 61/22<br>210/90 |
| 2013/0037977 | A1 * | 2/2013 | Burke | A61K 9/127<br>977/840 |
| 2014/0314653 | A1 * | 10/2014 | Thiriot | C01B 25/36<br>423/311 |
| 2016/0038432 | A1 * | 2/2016 | DeRosa | A61K 9/5015<br>514/44 R |
| 2016/0151284 | A1 * | 6/2016 | Heyes | A61K 48/0008<br>514/44 R |
| 2016/0213702 | A1 * | 7/2016 | von Maltzahn | A61K 31/716 |
| 2016/0235688 | A1 * | 8/2016 | Walsh | A61K 31/7105 |
| 2018/0133672 | A1 * | 5/2018 | Kim | B01L 3/502707 |
| 2019/0117572 | A1 * | 4/2019 | Tasciotti | A61K 9/0092 |
| 2019/0240354 | A1 * | 8/2019 | Abrams | A61K 48/0083 |
| 2020/0170949 | A1 * | 6/2020 | Spatz | A61K 9/1075 |
| 2020/0297634 | A1 * | 9/2020 | Karmali | A61K 47/69 |
| 2020/0306191 | A1 * | 10/2020 | Schariter | A61K 47/60 |
| 2021/0128474 | A1 * | 5/2021 | Strodiot | A61K 9/5123 |
| 2022/0133636 | A1 * | 5/2022 | Abrams | A61K 31/713<br>424/502 |
| 2022/0168234 | A1 * | 6/2022 | Bao | A61K 9/5192 |
| 2022/0378917 | A1 * | 12/2022 | Thomas | C07D 307/20 |
| 2022/0396548 | A1 * | 12/2022 | Jain | C07C 309/69 |
| 2023/0038598 | A1 * | 2/2023 | Staufer | C09B 67/0097 |
| 2023/0285297 | A1 * | 9/2023 | Smith | A61K 47/24 |
| 2023/0364638 | A1 * | 11/2023 | Kurdi | A61K 8/11 |
| 2024/0191238 | A1 * | 6/2024 | Wyss-Coray | C07K 16/24 |
| 2024/0246056 | A1 * | 7/2024 | Yazdan Panah | B01J 19/0046 |

FOREIGN PATENT DOCUMENTS

| | | |
|---|---|---|
| WO | WO 2012/170889 | 12/2012 |
| WO | WO 2013/093648 A2 | 6/2013 |
| WO | WO 2019/207060 | 10/2019 |

OTHER PUBLICATIONS

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, 3(5), (2016).

International Search Report for International PCT Application No. PCT/US2019/056936. Dated Oct. 18, 2019.

* cited by examiner

PUMPLESS ENCAPSULATION OF MESSENGER RNA

CROSS-REFERENCE TO RELATED APPLICATIONS

The present application is a 35 U.S.C. § 371 National Stage Application of International Application No. PCT/US19/56936, filed on Oct. 18, 2019, which claims priority to U.S. Provisional Application No. 62/747,838 filed Oct. 19, 2018, the disclosures of which are hereby incorporated by reference.

BACKGROUND

Messenger RNA therapy (MRT) is becoming an increasingly important approach for the treatment of a variety of diseases. MRT involves administration of messenger RNA (mRNA) into a patient in need thereof. The administered mRNA produces a protein encoded by the mRNA within the patient's body. Liposomes and/or lipid nanoparticles are commonly used to encapsulate mRNA for efficient in vivo delivery of mRNA. However, current methods for producing mRNA-loaded lipid nanoparticles suffer from poor encapsulation efficiency, low mRNA recovery and/or heterogeneous particle sizes. Another disadvantage to current methods is the need to use specialized equipment, such as gear pumps, peristaltic pumps and the like for the encapsulation process. Such specialized equipment may not be readily available in certain locations, such as patient-care settings.

SUMMARY OF INVENTION

The present invention provides, among other things, an improved process for lipid nanoparticle formulation and mRNA encapsulation. In particular, the present invention is based on the surprising discovery that a gravity-based mixing process for lipid encapsulation of nucleic acids allows for reproducible, highly efficient encapsulation efficiencies.

The present invention provides a cost effective, robust and user friendly mRNA encapsulation method that uses a gravity-based mixing process. Some of the benefits of a gravity-based mixing process for the encapsulation of nucleic acids include, for example, less variability, a pulseless flow of liquid allowing for precise, reproducible mixing flow rates without the need of machine-driven actuators. Other advantages of the gravity mixing process described herein include no calibrations or lengthy setups, cost efficiency, low maintenance and robust physical design (e.g. no moving parts and/or minimum accessories). The invention described herein provides, among other things, a scalable system which allows for multiple formulations that could be made at the same time independent of capacity and with minimal losses of material. Furthermore, the invention described herein provides for flexibility of process variables at least because the flow under gravity can be fine-tuned based on diameter of the flow path, which in turn allows for more flexibility with respect to flow rates.

Thus, in one aspect, the present invention provides a process of encapsulating messenger RNA (mRNA) in liposomes comprising a. providing a first stream comprising an mRNA solution at a first controlled flow rate, b. providing a second stream comprising a lipid solution at a second controlled flow rate, and c. mixing the first stream and the second stream to form mRNA-encapsulated liposomes, wherein the first controlled flow rate and the second controlled flow rate are achieved without use of a pump.

In another aspect, the present invention provides a process of encapsulating messenger RNA (mRNA) in liposomes comprising a. providing a first stream comprising mRNA solution at a first controlled flow rate, b. providing a second stream comprising a lipid solution at a second controlled flow rate, and c. mixing the first stream and the second stream to form mRNA-encapsulated liposomes, d. wherein each of steps a-c is performed under gravity feed and without external pressure.

In some embodiments, the process of claim 1 or 2, wherein the first stream is provided by a first conduit; and the second stream is provided by a second conduit, and wherein the first conduit and the second conduit are connected through a junction, thereby mixing the mRNA solution and the lipid solution.

In some embodiments, the junction comprises a T connector or a Y connector.

In some embodiments, the first conduit is connected to a first reservoir containing the mRNA solution and the second conduit is connected to a second reservoir containing the lipid solution.

In some embodiments, a first constriction controls the first controlled flow rate and a second constriction controls the second controlled flow rate.

In some embodiments, the first constriction and the second constriction provide controlled flow rates that are the same.

In some embodiments, the first constriction and the second constriction provide controlled flow rates that are different.

In some embodiments, the first controlled flow rate to second control flow rate is at a ratio of about 1.0×. In some embodiments, the first controlled flow rate to second control flow rate is at a ratio of about 1.2×. In some embodiments, the first controlled flow rate to second control flow rate is at a ratio of about 1.5×. In some embodiments, the first controlled flow rate to second control flow rate is at a ratio of about 1.8×. In some embodiments, the first controlled flow rate to second control flow rate is at a ratio of about 2.0×. In some embodiments, the first controlled flow rate to second control flow rate is at a ratio of about 2.5×. In some embodiments, the first controlled flow rate to second control flow rate is at a ratio of about 3.0×. In some embodiments, the first controlled flow rate to second control flow rate is at a ratio of about 1.0× or greater. In some embodiments, the first controlled flow rate to second control flow rate is at a ratio of about 1.2× or greater. In some embodiments, the first controlled flow rate to second control flow rate is at a ratio of about 1.5× or greater. In some embodiments, the first controlled flow rate to second control flow rate is at a ratio of about 1.8× or greater. In some embodiments, the first controlled flow rate to second control flow rate is at a ratio of about 2.0× or greater. In some embodiments, the first controlled flow rate to second control flow rate is at a ratio of about 2.5× or greater. In some embodiments, the first controlled flow rate to second control flow rate is at a ratio of about 3.0× or greater. In some embodiments, the first controlled flow rate to second control flow rate is at a ratio of about 3.5× or greater. In some embodiments, the first controlled flow rate to second control flow rate is at a ratio of about 4.0× or greater.

In some embodiments, the second controlled flow rate to first control flow rate is at a ratio of about 1.0×. In some embodiments, the second controlled flow rate to first control flow rate is at a ratio of about 1.2×. In some embodiments, the second controlled flow rate to first control flow rate is at a ratio of about 1.5×. In some embodiments, the second controlled flow rate to first control flow rate is at a ratio of about 1.8×. In some embodiments, the second controlled flow rate to first control flow rate is at a ratio of about 2.0×. In some embodiments, the second controlled flow rate to first control flow rate is at a ratio of about 2.5×. In some embodiments, the second controlled flow rate to first control flow rate is at a ratio of about 3.0×. In some embodiments, the second controlled flow rate to first control flow rate is at a ratio of about 1.0× or greater. In some embodiments, the second controlled flow rate to first control flow rate is at a ratio of about 1.2× or greater. In some embodiments, the second controlled flow rate to first control flow rate is at a ratio of about 1.5× or greater. In some embodiments, the second controlled flow rate to first control flow rate is at a ratio of about 1.8× or greater. In some embodiments, the second controlled flow rate to first control flow rate is at a ratio of about 2.0× or greater. In some embodiments, the second controlled flow rate to first control flow rate is at a ratio of about 2.5× or greater. In some embodiments, the second controlled flow rate to first control flow rate is at a ratio of about 3.0× or greater. In some embodiments, the second controlled flow rate to first control flow rate is at a ratio of about 3.5× or greater. In some embodiments, the second controlled flow rate to first control flow rate is at a ratio of about 4.0× or greater.

In some embodiments, the first constriction comprises a first diameter of the first conduit and the second constriction comprises a second diameter of the second conduit.

In some embodiments, the first constriction comprises a first diameter of a first reservoir and the second constriction comprises a second diameter of a second reservoir.

In some embodiments, the first constriction comprises a first diameter of a first reservoir-conduit connection and the second constriction comprises a second diameter of a second reservoir-conduit connection.

In some embodiments, the first constriction comprises a first diameter of a first conduit-junction connection and the second constriction comprises a second diameter of a second conduit-junction connection. The process of any of claims 7-10, wherein the first diameter is identical to the second diameter.

In some embodiments, the first diameter is different from the second diameter.

In some embodiments, the first diameter is larger than the second diameter.

In some embodiments, the first diameter is larger than the second diameter by 1.2×, 1.5×, 1.8×, 2.0×, 2.5×, by 1.2× or greater, 1.5× or greater, 1.8× or greater, 2.0× or greater, 2.5× or greater. In some embodiments, the first diameter is larger than the second diameter by about 3.0×, 3.5×, 4.0×, 4.5×, 5.0×, 5.5×, 6.0 or greater.

In some embodiments, the first diameter is larger than the second diameter in an amount that provides a first controlled flow rate to second controlled flow rate ratio that is 1:1, 2:1, 3:1, 4:1, 5:1, 10:1, 1:1 or greater, 2:1 or greater, 3:1 or greater, or 4:1 or greater, or 5:1 or greater, or 10:1 or greater.

In some embodiments, the first diameter of the first conduit is selected from the following ranges: 0.1 mm-1 mm, 1 mm-100 mm, 100 mm-1 cm, 1 cm-100 cm.

In some embodiments, the second diameter of the second conduit is selected from the following ranges: 0.1 mm-1 mm, 1 mm-100 mm, 100 mm-1 cm, 1 cm-100 cm.

In some embodiments, the first controlled flow rate ranges from about 0.1-1 mL/min, 1-150 mL/min, 150-250 mL/min, 250-500 mL/min, 500-1000 mL/min, 1000-2000 mL/min, 2000-3000 mL/min, 3000-4000 mL/min, or 4000-5000 mL/min.

In some embodiments, the first controlled flow rate is about 50 mL/min. In some embodiments, the first controlled flow rate is about 100 mL/min. In some embodiments, the first controlled flow rate is about 150 mL/min. In some embodiments, the first controlled flow rate is about 200 mL/min. In some embodiments, the first controlled flow rate is about 250 mL/min. In some embodiments, the first controlled flow rate is about 300 mL/min. In some embodiments, the first controlled flow rate is about 400 mL/min. In some embodiments, the first controlled flow rate is about 500 mL/min.

In some embodiments, the second controlled flow rate ranges from about 0.1-1 mL/min, 1-150 mL/min, 150-250 mL/min, 250-500 mL/min, 500-1000 mL/min, 1000-2000 mL/min, 2000-3000 mL/min, 3000-4000 mL/min, or 4000-5000 mL/min.

In some embodiments, the second controlled flow rate is about 10 mL/min. In some embodiments, the second controlled flow rate is about 50 mL/min. In some embodiments, the second controlled flow rate is about 100 mL/min. In some embodiments, the second controlled flow rate is about 150 mL/min. In some embodiments, the second controlled flow rate is about 200 mL/min. In some embodiments, the second controlled flow rate is about 250 mL/min. In some embodiments, the second controlled flow rate is about 300 mL/min. In some embodiments, the second controlled flow rate is about 400 mL/min. In some embodiments, the second controlled flow rate is about 500 mL/min.

In some embodiments, the lipid solution comprises one or more cationic lipids, one or more helper lipids, and one or more PEG-modified lipids.

In some embodiments, the lipid solution further comprises one or more cholesterol-based lipids.

In some embodiments, the one or more cholesterol-based lipids are cholesterol and/or PEGylated cholesterol.

In some embodiments, the lipid solution comprises pre-formed lipid nanoparticles.

In some embodiments, the lipid solution is a suspension of pre-formed lipid nanoparticles.

In some embodiments, the first stream comprises about 50% water or greater and the second stream comprises about 50% ethanol or greater.

In some embodiments, the first stream comprises about 85-99% water and the second stream comprises about 85-99% ethanol.

In some embodiments, each of the first stream and the second stream comprises 50% water or greater.

In some embodiments, the process results in lipid nanoparticles have a size ranging from about 40-150 nm.

In some embodiments, about 50%, 55%, 60%, 65%, 70%, 75%, 80%, 85%, 90%, 95%, 96%, 97%, 98%, 99%, or 100% of the lipid nanoparticles have a size of 150 nm or less.

In some embodiments, about 50%, 55%, 60%, 65%, 70%, 75%, 80%, 85%, 90%, 95%, 96%, 97%, 98%, 99%, or 100% of the lipid nanoparticles have a size of 100 nm or less.

In some embodiments, greater than about 70%, 75%, 80%, 85%, 90%, 95%, 96%, 97%, 98%, 99% of the lipid nanoparticles have a size ranging from 50-80 nm.

In some embodiments, the process results in an encapsulation efficiency of at least about 60%. In some embodiments, the process results in an encapsulation efficiency of at least about 65%. In some embodiments, the process results in an encapsulation efficiency of at least about 70%. In some embodiments, the process results in an encapsulation efficiency of at least about 75%. In some embodiments, the process results in an encapsulation efficiency of at least about 80%. In some embodiments, the process results in an encapsulation efficiency of at least about 85%. In some embodiments, the process results in an encapsulation efficiency of at least about 90%. In some embodiments, the process results in an encapsulation efficiency of at least about 95%. In some embodiments, the process results in an encapsulation efficiency of at least about 96%. In some embodiments, the process results in an encapsulation efficiency of at least about 97%. In some embodiments, the process results in an encapsulation efficiency of at least about 98%. In some embodiments, the process results in an encapsulation efficiency of at least about 99%.

In some embodiments, the process results in at least about 50% recovery of mRNA. In some embodiments, the process results in at least about 55% recovery of mRNA. In some embodiments, the process results in at least about 60% recovery of mRNA. In some embodiments, the process results in at least about 65% recovery of mRNA. In some embodiments, the process results in at least about 70% recovery of mRNA. In some embodiments, the process results in at least about 75% recovery of mRNA. In some embodiments, the process results in at least about 80% recovery of mRNA. In some embodiments, the process results in at least about 85% recovery of mRNA. In some embodiments, the process results in at least about 90% recovery of mRNA. In some embodiments, the process results in at least about 95% recovery of mRNA. In some embodiments, the process results in at least about 96% recovery of mRNA. In some embodiments, the process results in at least about 97% recovery of mRNA. In some embodiments, the process results in at least about 98% recovery of mRNA. In some embodiments, the process results in at least about 99% recovery of mRNA.

In some embodiments, the process results in at least 0.1 mg of encapsulated mRNA. In some embodiments, the process results in at least 0.5 mg of encapsulated mRNA. In some embodiments, the process results in at least 1 mg of encapsulated mRNA. In some embodiments, the process results in at least 5 mg of encapsulated mRNA. In some embodiments, the process results in at least 10 mg of encapsulated mRNA. In some embodiments, the process results in at least 100 mg of encapsulated mRNA. In some embodiments, the process results in at least 500 mg of encapsulated mRNA. In some embodiments, the process results in at least 1,000 mg of encapsulated mRNA.

In some embodiments, the process results in lipid nanoparticles that do not require further purification.

In some embodiments, the process further comprises a step of collecting lipid nanoparticles in a receptacle or conduit.

In some embodiments, the mRNA is codon-optimized.

In some embodiments, the mRNA is unmodified.

In some embodiments, the mRNA is modified.

In some embodiments, the process includes multiple pairs of first streams and corresponding second streams.

In some embodiments, in step c the mixing of each of the pair of first and second streams occurs simultaneously.

In some embodiments, the process comprises at least 10, 20, 30, 40, 50, 100, 150, 200 pairs of the first streams and the second stream.

In some embodiments, each individual first stream provides a different mRNA solution.

In some embodiments, at least a subset of first streams provides a same mRNA solution.

In some embodiments, each individual second stream provides a different lipid solution.

In some embodiments, at least a subset of second streams provide a same lipid solution.

In another aspect, the present invention provides a method of delivering mRNA for in vivo protein production comprising administering into a subject a composition of lipid nanoparticles encapsulating mRNA generated by a process of any one of the preceding claims.

In another aspect, the present invention provides a system for encapsulating messenger RNA (mRNA) in lipid nanoparticles comprising a first conduit for providing an mRNA solution at a first controlled flow rate, and a second conduit for providing a lipid solution at a second controlled flow rate, wherein the first conduit and the second conduit are connected through a junction to facilitate mixing of the mRNA solution and the lipid solution, and wherein the first controlled flow rate and the second controlled flow rate are achieved without use of a pump.

In some embodiments, the junction comprises a T connector or a Y connector.

In some embodiments, the first conduit is connected to a first reservoir for containing the mRNA solution and the second conduit is connected to a second reservoir for containing the lipid solution.

In some embodiments, the first conduit has a first diameter and the second conduit has a second diameter.

In some embodiments, the first diameter is identical to the second diameter.

In some embodiments, the first diameter is different from the second diameter.

In some embodiments, the first dimeter is larger than the second diameter.

In some embodiments, the first diameter of the first conduit is selected from the following ranges: 0.1 mm-1 mm, 1 mm-100 mm, 100 mm-1 cm, 1 cm-100 cm.

In some embodiments, the second diameter of the second conduit is selected from the following ranges: 0.1 mm-1 mm, 1 mm-100 mm, 100 mm-1 cm, 1 cm-100 cm.

In some embodiments, the system further comprises a receptacle or conduit to collect resulting lipid nanoparticles.

Other features, objects, and advantages of the present invention are apparent in the detailed description, drawings and claims that follow. It should be understood, however, that the detailed description, the drawings, and the claims, while indicating embodiments of the present invention, are given by way of illustration only, and should not be construed as being limiting. Various changes and modifications within the scope of the invention will become apparent to those skilled in the art.

BRIEF DESCRIPTION OF THE DRAWINGS

The drawings are for illustration purposes only and not for limitation.

FIG. 3A depicts a conduit that has a large diameter. FIG. 3B depicts a conduit that has a small diameter.

FIG. 4, panel A depicts a Reservoir, conduit and junction that does not have a constrictor. FIG. 4, panel B depicts a reservoir and a conduit, in which the conduit has a constrictor attached. FIG. 4, panel C depicts a reservoir and a conduit in which the conduit has a constrictor attached near the junction. FIG. 4, panel D depicts a reservoir and a conduit in which a constrictor is placed over the reservoir.

FIG. 5A shows a reservoir, conduit and junction, in which the junction is in an upwards position. This upwards position prevents flow of liquid and allows the lines to purge. FIG. 5B depicts a reservoir, conduit and junction, in which the junction is in an extended position. This downward position allows the conduits to fill with liquid and be mixed at the junction.

DEFINITIONS

Figure 1:
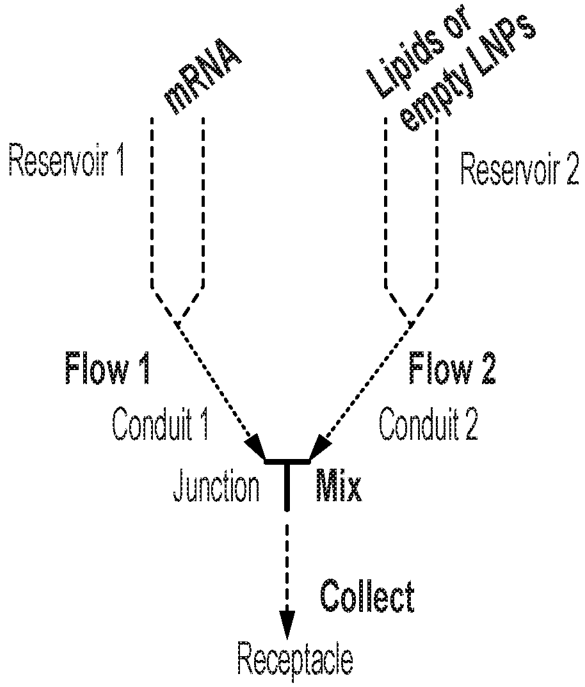
FIG. 1 is a schematic of a pumpless nucleic acid lipid nanoparticle encapsulation process. The schematic depicts Reservoir 1 which houses a nucleic acid solution (mRNA), Reservoir 2 which houses lipids or empty lipid nanoparticles (LNPs), Conduits 1 and Conduit 2 though which liquid from Reservoirs 1 and 2 flow, respectively. The flow from Conduit 1 (Flow 1) and from Conduit 2 (Flow 2) meet and mix at the junction (depicted as a T-junction). Upon mixing, the encapsulated nucleic acid is collected in a receptacle.

In order for the present invention to be more readily understood, certain terms are first defined below. Additional definitions for the following terms and other terms are set forth throughout the specification.

Alkyl: As used herein, "alkyl" refers to a radical of a straight-chain or branched saturated hydrocarbon group having from 1 to 20 carbon atoms ("$C_{1-20}$ alkyl"). In some embodiments, an alkyl group has 1 to 3 carbon atoms ("$C_{1-3}$ alkyl"). Examples of $C_{1-3}$ alkyl groups include methyl ($C_1$), ethyl ($C_2$), n-propyl ($C_3$), and isopropyl ($C_3$). In some embodiments, an alkyl group has 8 to 12 carbon atoms ("$C_{8-12}$ alkyl"). Examples of $C_{8-12}$ alkyl groups include, without limitation, n-octyl ($C_8$), n-nonyl ($C_9$), n-decyl ($C_{10}$), n-undecyl ($C_{11}$), n-dodecyl ($C_{12}$) and the like. The prefix "n-" (normal) refers to unbranched alkyl groups. For example, n-$C_8$ alkyl refers to $-(CH_2)_7CH_3$, n-$C_{10}$ alkyl refers to $-(CH_2)_9CH_3$, etc.

Amino acid: As used herein, term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Atmospheric pressure: As used herein, the term "atmospheric pressure" means the pressure exerted by the weight of the atmosphere, which at sea level has a mean value of about 101,325 pascals.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Encapsulation: As used herein, the term "encapsulation," or grammatical equivalent, refers to the process of confining an individual mRNA molecule within a nanoparticle.

Gravity Feed: As used herein, the term "gravity feed" means using gravity to move a substance (e.g. a liquid) from one place to another without the use of a pump.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" refers to a polynucleotide that encodes at least one peptide, polypeptide or protein. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Pump: As used herein, the term "pump" refers to a device for driving or compressing fluids or gases. Multiple kinds of "pumps" are known, and include for example diaphragm pumps, centrifugal pumps, piston pumps, peristaltic pumps, pulse pumps and lobe pumps. Pumps may include mechanically actuated devices and/or manually actuated devices.

Salt: As used herein, the term "salt" refers to an ionic compound that does or may result from a neutralization reaction between an acid and a base.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Yield: As used herein, the term "yield" refers to the percentage of mRNA recovered after encapsulation as compared to the total mRNA as starting material. In some embodiments, the term "recovery" is used interchangeably with the term "yield".

Various aspects of the invention are described in detail in the following sections. The use of sections is not meant to limit the invention. Each section can apply to any aspect of the invention. In this application, the use of "or" means "and/or" unless stated otherwise.

DETAILED DESCRIPTION

The present invention provides, among other things, an improved process for lipid nanoparticle formulation and nucleic acid encapsulation. The present invention is, in part, based on the surprising discovery that nucleic acid encapsulation can be reproducibly performed at atmospheric pressure using gravity to control lipid and nucleic acid mixing rates to produce encapsulated nucleic acids. Using gravity in this way, the mixing can be performed without use of pumps or external pressure (e.g. pump pressure), other than atmospheric pressure. Accordingly, the pressures that are used to control the flow rate of the process described herein are atmospheric pressure and head pressure (e.g. pressure in a tube and reservoir). The encapsulation process provided herein ensures stability of nucleic acids, including for example mRNA, and results in high encapsulation efficiencies (e.g. about between 75 and 95% or more encapsulation efficiencies).

The encapsulation process described herein allows for use of the process in various settings, for example in large-scale commercial process manufacturing where large volumes of pressurized liquids such as ethanol may pose safety and handling concerns. Other uses of the encapsulation process disclosed herein include "bedside" commercial process manufacturing, for example, in the preparation of smallscale commercial products on site such as in a hospital pharmacy. In yet another use, the process described herein can be used in a commercial process manufacturing setting in locations where expensive equipment and maintenance may be challenging. In yet another example of use, the process described herein can be used in the high-throughput preparation of encapsulated nucleic acids, for example for screening purposes, where purchase, calibration and maintenance of large numbers of pumps and other machinery inhibit quick and high-throughput testing.

The encapsulation process described herein can be applied to various other methods of encapsulating mRNA in lipid nanoparticles described in the art. As used herein, Process A refers to a conventional method of encapsulating mRNA by mixing mRNA with a mixture of lipids, without first pre-forming the lipids into lipid nanoparticles. As used herein, Process B refers to a process of encapsulating messenger RNA (mRNA) by mixing pre-formed lipid nanoparticles with mRNA. As compared to Process B, Process A does not involve pre-formation of lipid nanoparticles. Process A and Process B include those described in WO2016004318 and WO2018089801, respectively, which are hereby incorporated by reference. In some embodiments, the encapsulation process described herein can be used to make empty lipid nanoparticles.

Accordingly, the invention provided herein allows for highly efficient, reproducible lipid encapsulation of nucleic acids at various scales and settings by the use of a gravity-based mixing process to produce encapsulated nucleic acids.

Gravity-Based Encapsulation of Nucleic Acids

In one aspect of the disclosure, a process of encapsulating a nucleic acid in liposomes is provided. In some embodiments, the encapsulation process includes 1) a first reservoir to provide a desired nucleic acid in aqueous solution; 2) a second reservoir to provide a solution of lipids and/or lipid nanoparticles (LNPs); 3) conduits for the first and second reservoirs to allow for flow of nucleic acids, and lipids and/or LNPs; 4) a junction for mixing the nucleic acids and lipids and/or LNPs; and 5) a receptacle or conduit for collecting the mixed/encapsulated nucleic acids in LNPs. A schematic of an exemplary process of encapsulating a nucleic acid is shown in FIG. 1.

In some embodiments, the encapsulation process includes 1) a first reservoir to provide an mRNA solution; 2) a second reservoir to provide a solution of lipids and/or lipid nanoparticles (LNPs); 3) conduits for the first and the second reservoirs to allow for flow of the mRNA solution, and the lipids and/or LNPs; 4) a junction for mixing the mRNA and lipids and/or LNPs; and 5) a receptacle or conduit for collecting the mixed the mixed encapsulated mRNA in LNPs.

In some embodiments, the encapsulated mRNA is suitable to deliver for in vivo protein production comprising administering into a subject a composition of lipid nanoparticles encapsulating mRNA generated by the process described herein. Accordingly, in some embodiments, a method is provided of delivering mRNA for in vivo protein production comprising administering into a subject a composition of lipid nanoparticles encapsulating mRNA generated by the process described herein.

In another aspect of the disclosure, the process described herein is used to create liposomal delivery vehicles, such as for example, a lipid nanoparticle (LNP) or a liposome. In some embodiments, the process includes 1) a reservoir to provide a solution of one or more kinds of lipids; 2) a second reservoir to provide an additional solution of one or more kind of lipids; 3) conduits for the first and the second reservoirs to allow for flow of the lipid solution; 4) a junction for mixing the lipids; and 5) a receptacle or conduit for collecting the created liposomal delivery vehicle. In some embodiments, the first and the second reservoirs have the same solution of one or more kinds of lipids.

In another aspect of the disclosure, a system for encapsulating nucleic acids is provided. Accordingly, in some embodiments, the system includes 1) a first reservoir to provide a desired nucleic acids in aqueous solution; 2) a second reservoir to provide a solution of lipids and/or lipid nanoparticles (LNPs); 3) conduits for the first and second reservoirs to allow for flow of nucleic acids, and lipids and/or LNPs; 4) a junction for mixing the nucleic acids and lipids and/or LNPs; and 5) a receptacle or conduit for collecting the mixed/encapsulated nucleic acids in LNPs.

Controlling Flow Rate in the Gravity-Based Encapsulation Process

Various manners of controlling liquid flow rate and the resulting mixing process to achieve reproducible encapsulation of nucleic acids are envisioned. In some embodiments, the liquid flow rate is controlled by adjusting the diameter of one or more of the reservoirs, conduits, and/or junctions. In embodiments, the diameter of the reservoirs, conduits, and/or junctions is controlled by the use of reservoirs, conduits and/or junctions of a specific diameter. In embodiments, the diameter of the reservoirs, conduits and/or junctions are adjusted by providing a constriction in one or more of the reservoirs, conduits and/or junctions.

Thus, in embodiments, the liquid flow rate and the mixing process are controlled by providing a constriction in the first and/or the second reservoir. In some embodiments, the liquid flow rate and the mixing process are controlled by providing a constriction at the reservoir-conduit connection. In some embodiments, the liquid flow rate and the mixing process are controlled by providing a constriction in a conduit associated with the first and/or second reservoir. In some embodiments, the liquid flow rate and the mixing process are controlled by providing a constriction at the conduit-junction connection. In some embodiments, the liquid flow rate and the mixing process are controlled by providing a constriction in the junction. Providing any one or more of the above constrictions allows for fine tuning the liquid flow rate and the mixing process.

In some embodiments, the liquid flow and mixing processes are controlled by adjustment of a diameter of one or more of the reservoirs, conduits, and/or junctions. Accordingly, in some embodiments the diameter of the first and/or the second reservoir is adjusted to a desired diameter, thus providing a first diameter associated with the first reservoir and a second diameter associated with the second reservoir. Any method to achieve the desired diameter is envisioned, including for example use of a reservoir manufactured to have a certain diameter, or placement of a constriction on a reservoir to achieve the desired diameter. In some embodiments, the diameter of the first reservoir is about between 1 cm-100 cm, 100 cm-1 dm, 1 dm-100 dm, 10 m-50 m. In some embodiments, the diameter of the second reservoir is between 1 cm-100 cm, 100 cm-1 dm, 1 dm-100 dm, 10 m-50 m. In some embodiments, the first and the second reservoir have the same diameter. In some embodiments, the first reservoir has a larger diameter than the second reservoir. In some embodiments, the second reservoir has a larger diameter than the first reservoir. In some embodiments, the diameter of the first reservoir is 1.2×, 1.5×, 1.8×, 2.0×, 2.5× or greater than the diameter of the second reservoir. In some embodiments, the diameter of the second reservoir is 1.2×, 1.5×, 1.8×, 2.0×, 2.5× or greater than the diameter of the second reservoir.

In some embodiments, the liquid flow and mixing processes are controlled by adjustment of a diameter of one or more of the conduits. In some embodiments, the process uses a first conduit and a second conduit as depicted in FIG. 1, thus providing a first diameter associated with the first conduit and a second diameter associated with the second conduit. The desired diameter of the first and the second conduits is achieved by any method known in the art, for example by use of a conduit having a specific manufactured diameter, or by placement of a constriction on a conduit to achieve a desired conduit diameter. In some embodiments, the diameter of a first conduit is about between 0.1 mm-1 mm, 1 mm-100 mm, 100 mm-1 cm, 1 cm-100 cm, 100 cm-1 dm, 1 dm-100 dm, 100 dm-1 m. In some embodiments, the first conduit is about between 0.1 mm-1 mm, 1 mm-100 mm, 100 mm-1 cm, 1 cm-100 cm. In some embodiments, the diameter of the second conduit is about between 0.1 mm-1 mm, 1 mm-100 mm, 100 mm-1 cm, 1 cm-100 cm, 100 cm-1 dm, 1 dm-100 dm, 100 dm-1 m. In some embodiments, the diameter of the second conduit is about between 0.1 mm-1 mm, 1 mm-100 mm, 100 mm-1 cm, and 1 cm-100 cm. In some embodiments, the first and the second conduit have the same diameter. In embodiments, the first conduit has a larger diameter than the second conduit. In embodiments, the second conduit has a larger diameter than the first conduit. In embodiments, the diameter of the first conduit is 1.2×, 1.5×, 1.8×, 2.0×, 2.5× or greater than the diameter of the second conduit. In embodiments, the diameter of the second conduit is 1.2×, 1.5×, 1.8×, 2.0×, 2.5× or greater than the diameter of the second conduit.

In some embodiments, the liquid flow and mixing processes are controlled by adjustment of a diameter at the reservoir-conduit junction. In some embodiments, the process has a first reservoir-conduit junction and a second reservoir-conduit junction associated with reservoir 1 and reservoir 2, respectively and as depicted in FIG. 1, thus providing a first diameter associated with the first reservoir-conduit junction and a second diameter associated with the second reservoir-conduit junction. The desired diameter of the first and the second reservoir-conduit junction is achieved by any method known in the art, for example by use of a reservoir-conduit junction having a specific manufactured diameter, or by placement of a constriction on a reservoir-conduit junction to achieve a desired reservoir-conduit junction diameter. In some embodiments, the diameter of a first reservoir-conduit junction is about between 0.1 mm-1 mm, 1 mm-100 mm, 100 mm-1 cm, 1 cm-100 cm, 100 cm-1 dm, 1 dm-100 dm, 100 dm-1 m. In some embodiments, the first reservoir-conduit is about between 0.1 mm-1 mm, 1 mm-100 mm, 100 mm-1 cm, 1 cm-100 cm. In some embodiments, the diameter of the second reservoir-conduit is about between 0.1 mm-1 mm, 1 mm-100 mm, 100 mm-1 cm, 1 cm-100 cm, 100 cm-1 dm, 1 dm-100 dm, 100 dm-1 m. In some embodiments, the diameter of the second reservoir-conduit is about between 0.1 mm-1 mm, 1 mm-100 mm, 100 mm-1 cm, and 1 cm-100 cm. In some embodiments, the first and the second reservoir-conduit have the same diameter. In some embodiments, the first reservoir-conduit has a larger diameter than the second reservoir-conduit. In some embodiments, the second reservoir-conduit has a larger diameter than the first reservoir-conduit. In some embodiments, the diameter of the first reservoir-conduit is 1.2×, 1.5×, 1.8×, 2.0×, 2.5× or greater than the diameter of the second reservoir-conduit. In some embodiments, the diameter of the second reservoir-conduit is 1.2×, 1.5×, 1.8×, 2.0×, 2.5× or greater than the diameter of the second reservoir-conduit.

In some embodiments, the liquid flow and mixing processes are controlled by adjustment of a diameter at the junction. In some embodiments, the junction is a T-shaped connector or a Y-shaped connector. In some embodiments, the junction is a T-shaped connector. In some embodiments, the junction is a Y-shaped connector. In some embodiments, the process has a junction that has a first diameter which connects to the first conduit, and the junction has a second diameter which connects to the second conduit. The junction and the associated connections with the first and the second conduits are depicted in FIG. 1. The desired diameter of the first and the second diameter of the junction is achieved by any method known in the art, for example by use of a junction having a specific manufactured first and/or second diameter, or by placement of a constriction at the first and/or the second diameter of the junction to achieve a desired reservoir-conduit junction diameter. In some embodiments, the first diameter of the junction is about between 0.1 mm-1 mm, 1 mm-100 mm, 100 mm-1 cm, 1 cm-100 cm, 100 cm-1 dm, 1 dm-100 dm, 100 dm-1 m. In some embodiments, the first diameter of the junction is about between 0.1 mm-1 mm, 1 mm-100 mm, 100 mm-1 cm, 1 cm-100 cm. In some embodiments, the second diameter of the junction is about between 0.1 mm-1 mm, 1 mm-100 mm, 100 mm-1 cm, 1 cm-100 cm, 100 cm-1 dm, 1 dm-100 dm, 100 dm-1 m. In some embodiments, the second diameter of the junction is about between 0.1 mm-1 mm, 1 mm-100 mm, 100 mm-1 cm, and 1 cm-100 cm. In some embodiments, the first and second diameter of the junction are the same. In some embodiments, the first diameter of the junction has a larger diameter than the second diameter of the junction. In some embodiments, the second diameter of the junction has a larger diameter than the first diameter of the junction. In some embodiments, the first diameter of the junction is 1.2×, 1.5×, 1.8×, 2.0×, 2.5× or greater than the diameter of the second diameter of the junction. In some embodiments, the diameter of the second diameter of the junction is 1.2×, 1.5×, 1.8×, 2.0×, 2.5× or greater than the diameter of the second diameter of the junction.

Adjusting the first and second diameters as described above allows for a controlled flow rate and thus a controlled mixing process. Adjustment of the first diameter allows for a resultant first flow rate, and an adjustment of the second diameter allows for a resultant second flow rate. In some embodiments, the first diameter is identical to the second diameter. In some embodiments, the first diameter is different than the second diameter. In some embodiments, the first diameter is larger than the second diameter. In some embodiments, the first diameter is larger than the second diameter in an amount that provides a first controlled flow rate to second controlled flow rate. In some embodiments, the first controlled flow rate to second controlled flow rate ratio is about 1:1, 2:1, 3:1, 4:1, 5:1, 10:1, 1:1 or greater, 2:1 or greater, 3:1 or greater, or 4:1 or greater, or 5:1 or greater, or 10:1 or greater. In some embodiments, the first controlled flow rate to second controlled flow rate ratio is about 1:1. In some embodiments, the first controlled flow rate to second controlled flow rate ratio is about 1:1 or greater. In some embodiments, the first controlled flow rate to second controlled flow rate ratio is about 2:1. In some embodiments, the first controlled flow rate to second controlled flow rate ratio is about 2:1 or greater. In some embodiments, the first controlled flow rate to second controlled flow rate ratio is about 3:1. In some embodiments, the first controlled flow rate to second controlled flow rate ratio is about 3:1 or greater. In some embodiments, the first controlled flow rate to second controlled flow rate ratio is about 4:1. In some embodiments, the first controlled flow rate to second controlled flow rate ratio is about 4:1 or greater. In some embodiments, the first controlled flow rate to second controlled flow rate ratio is about 5:1. In some embodiments, the first controlled flow rate to second controlled flow rate ratio is about 5:1 or greater. In some embodiments, the first controlled flow rate to second controlled flow rate ratio is about 10:1. In some embodiments, the first controlled flow rate to second controlled flow rate ratio is about 10:1 or greater. In some embodiments, the first controlled flow rate to second controlled flow rate ratio for Process A is about 1:1. In some embodiments, the first controlled flow rate to second controlled flow rate ratio for Process A is about 2:1. In some embodiments, the first controlled flow rate to second controlled flow rate ratio for Process A is about 3:1. In some embodiments, the first controlled flow rate to second controlled flow rate ratio for Process A is about 4:1. In some embodiments, the first controlled flow rate to second controlled flow rate ratio for Process A is about 5:1. In some embodiments, the first controlled flow rate to second controlled flow rate ratio for Process A is about 1:1. In some embodiments, the first controlled flow rate to second controlled flow rate ratio for Process B is about 1:1. In some embodiments, the first controlled flow rate to second controlled flow rate ratio for Process B is about 2:1. In some embodiments, the first controlled flow rate to second controlled flow rate ratio for Process B is about 3:1. In some embodiments, the first controlled flow rate to second controlled flow rate ratio for Process B is about 4:1.

In some embodiments, the second diameter is larger than the first diameter in an amount that provides a first controlled flow rate to second controlled flow rate. In some embodiments, the second controlled flow rate to first controlled flow rate ratio is about 1:1, 2:1, 3:1, 4:1, 5:1, 10:1, 1:1 or greater, 2:1 or greater, 3:1 or greater, or 4:1 or greater, or 5:1 or greater, or 10:1 or greater. In some embodiments, the second controlled flow rate to first controlled flow rate ratio is about 1:1. In some embodiments, the second controlled flow rate to first controlled flow rate ratio is about 1:1 or greater. In some embodiments, the second controlled flow rate to first controlled flow rate ratio is about 2:1. In some embodiments, the second controlled flow rate to first controlled flow rate ratio is about 2:1 or greater. In some embodiments, the second controlled flow rate to first controlled flow rate ratio is about 3:1. In some embodiments, the second controlled flow rate to first controlled flow rate ratio is about 3:1 or greater. In some embodiments, the second controlled flow rate to first controlled flow rate ratio is about 4:1. In some embodiments, the second controlled flow rate to first controlled flow rate ratio is about 4:1 or greater. In some embodiments, the second controlled flow rate to first controlled flow rate ratio is about 5:1. In some embodiments, the second controlled flow rate to first controlled flow rate ratio is about 5:1 or greater. In some embodiments, the second controlled flow rate to first controlled flow rate ratio is about 10:1. In some embodiments, the second controlled flow rate to first controlled flow rate ratio is about 10:1 or greater.

Adjustment of the diameters as described herein is used to produce a controlled flow rate to achieve a desired mixing of the nucleic acids with lipids. In some embodiments, a first controlled flow rate is achieved in which the flow rate is about 0.1-1 mL/min, 1-150 mL/min, 150-250 mL/min, 250-500 mL/min, 500-1000 mL/min, 1000-2000 mL/min, 2000-3000 mL/min, 3000-4000 mL/min or 4000-5000 mL/min. In some embodiments, the first controlled flow rate is about 0.1-1 mL/min. In some embodiments, the first controlled flow rate is about 1-150 mL/min. In some embodiments, the first controlled flow rate is about 150-250 mL/min. In some embodiments, the first controlled flow rate is about 250-500 mL/min. In some embodiments, the first controlled flow rate is about 500-1000 mL/min. In some embodiments, the first controlled flow rate is about 1000-2000 mL/min. In some embodiments, the first controlled flow rate is about 2000-3000 mL/min. In some embodiments, the first controlled flow rate is about 3000-4000 mL/min. In some embodiments, the first controlled flow rate is about 4000-5000 mL/min. In some embodiments, the first controlled flow rate is about between 150 and 250 mL/min (e.g. about 150 mL/min, 155 mL/min, 160 mL/min, 165 mL/min, 170 mL/min, 175 mL/min, 180 mL/min, 185 mL/min, 190 mL/min, 195 mL/min, 200 mL/min, 205 mL/min, 210 mL/min, 215 mL/min, 220 mL/min, 225 mL/min, 230 mL/min, 235 mL/min, 240 mL/min, 245 mL/min, or 250 mL/min).

In some embodiments, a second controlled flow rate is achieved in which the flow rate is about 0.1-1 mL/min, 1-150 mL/min, 150-250 mL/min, 250-500 mL/min, 500-1000 mL/min, 1000-2000 mL/min, 2000-3000 mL/min, 3000-4000 mL/min or 4000-5000 mL/min. In some embodiments, the second controlled flow rate is about 0.1-1 mL/min. In some embodiments, the second controlled flow rate is about 1-150 mL/min. In some embodiments, the second controlled flow rate is about 150-250 mL/min. In some embodiments, the second controlled flow rate is about 250-500 mL/min. In some embodiments, the second controlled flow rate is about 500-1000 mL/min. In some embodiments, the second controlled flow rate is about 1000-2000 mL/min. In some embodiments, the second controlled flow rate is about 2000-3000 mL/min. In some embodiments, the second controlled flow rate is about 3000-4000 mL/min. In some embodiments, the second controlled flow rate is about 4000-5000 mL/min. In some embodiments, the second controlled flow rate is about between 25 and 75 mL/min (e.g. about 25 mL/min, 26 mL/min, 27 mL/min, 28 mL/min, 29 mL/min, 30 mL/min, 31 mL/min. 32 mL/min, 33 mL/min, 34 mL/min, 35 mL/min, 36 mL/min, 37 mL/min, 38 mL/min, 39 mL/min, 40 mL/min, 41 mL/min, 42 mL/min, 43 mL/min, 44 mL/min, 45 mL/min, 46 mL/min, 47 mL/min, 48 mL/min, 49 mL/min, 50 mL/min, 51 mL/min, 52 mL/min, 53 mL/min, 54 mL/min, 55 mL/min, 56 mL/min, 57 mL/min, 58 mL/min, 59 mL/min, 60 mL/min, 61 mL/min, 62 mL/min, 63 mL/min, 64 mL/min, 65 mL/min, 66 mL/min, 67 mL/min, 68 mL/min, 69 mL/min, 70 mL/min, 71 mL/min, 72 mL/min, 73 mL/min, 74 mL/min, or 75 mL/min) In some embodiments, the first controlled flow rate is about 50 mL/min.

In some embodiments, the first controlled flow rate to second controlled flow rate is at a ratio of about 1:1, 2:1, 3:1, 4:1, 5:1, 10:1, 1:1 or greater, 2:1 or greater, 3:1 or greater, or 4:1 or greater, or 5:1 or greater, or 10:1 or greater. Accordingly, in some embodiments, the first controlled flow rate to second controlled flow rate is at a ratio of about 1:1. In some embodiments, the first controlled flow rate to second controlled flow rate is at a ratio of about 2:1. In some embodiments, the first controlled flow rate to second controlled flow rate is at a ratio of about 3:1. In some embodiments, the first controlled flow rate to second controlled flow rate is at a ratio of about 4:1. In some embodiments, the first controlled flow rate to second controlled flow rate is at a ratio of about 5:1. In some embodiments, the first controlled flow rate to second controlled flow rate is at a ratio of about 10:1. In some embodiments, the first controlled flow rate to second controlled flow rate is at a ratio of about 1:1 or greater. In some embodiments, the first controlled flow rate to second controlled flow rate is at a ratio of about 2:1 or greater. In some embodiments, the first controlled flow rate to second controlled flow rate is at a ratio of about 3:1 or greater. In some embodiments, the first controlled flow rate to second controlled flow rate is at a ratio of about 4:1 or greater. In some embodiments, the first controlled flow rate to second controlled flow rate is at a ratio of about 5:1 or greater. In some embodiments, the first controlled flow rate to second controlled flow rate is at a ratio of about 10:1 or greater.

In some embodiments, the second controlled flow rate to first controlled flow rate is at a ratio of about 1:1, 2:1, 3:1, 4:1, 5:1, 10:1, 1:1 or greater, 2:1 or greater, 3:1 or greater, or 4:1 or greater, or 5:1 or greater, or 10:1 or greater. Accordingly, in some embodiments, the second controlled flow rate to first controlled flow rate is at a ratio of about 1:1. In some embodiments, the second controlled flow rate to first controlled flow rate is at a ratio of about 2:1. In some embodiments, the second controlled flow rate to first controlled flow rate is at a ratio of about 3:1. In some embodiments, the second controlled flow rate to first controlled flow rate is at a ratio of about 4:1. In some embodiments, t the second controlled flow rate to first controlled flow rate is at a ratio of about 5:1. In some embodiments, the second controlled flow rate to first controlled flow rate is at a ratio of about 10:1. In some embodiments, the second controlled flow rate to first controlled flow rate is at a ratio of about 1:1 or greater. In some embodiments, the second controlled flow rate to first controlled flow rate is at a ratio of about 2:1 or greater. In some embodiments, the second controlled flow rate to first controlled flow rate is at a ratio of about 3:1 or greater. In some embodiments, the second controlled flow rate to first controlled flow rate is at a ratio of about 4:1 or greater. In some embodiments, the second controlled flow rate to first controlled flow rate is at a ratio of about 5:1 or greater. In some embodiments, the second controlled flow rate to first controlled flow rate is at a ratio of about 10:1 or greater.

In some embodiments, a first flow rate is controlled and a second flow rate is not controlled. For example, in some embodiments, one flow stream is mixed with controlled flow rate into a reservoir containing a desired component. Thus, in some embodiments a flow rate stream of a nucleic acid solution is controlled. In some embodiments, a flow rate stream of a lipid solution or LNP is controlled. In some embodiments, the flow rate stream of a nucleic acid solution is controlled and the flow rate stream of a lipid solution or LNP is controlled. In some embodiments, the first flow comprises a nucleotide. In some embodiments, the second flow comprises a lipid solution or LNP. In some embodiments, the first flow and the second flow comprise a nucleic acid. In some embodiments, the nucleic acid can be DNA or RNA. In some embodiments, the first flow and the second flow comprise a lipid solution or a LNP.

Gravity-Based Encapsulation Process—Controlled Mixing

In some embodiments, a lipid solution containing dissolved lipids, and an aqueous or buffer solution are mixed into a solution such that the lipids can form nanoparticles without mRNA (or empty preformed lipid nanoparticles). In some embodiments, an mRNA solution and a preformed lipid nanoparticle solution are mixed into a solution such that the mRNA becomes encapsulated in the lipid nanoparticle. Such a solution is also referred to as a formulation or encapsulation solution. A suitable formulation or encapsulation solution includes a solvent such as ethanol. For example, a suitable formulation or encapsulation solution includes about 10% ethanol, about 15% ethanol, about 20% ethanol, about 25% ethanol, about 30% ethanol, about 35% ethanol, or about 40% ethanol.

Controlling the flow rate in the process described herein allows for reproducible encapsulation of nucleic acids in lipids. The controlled flow rate in the process described herein also allows for reproducible production of lipid nanoparticles (LNPs). The controlled flow rate achieves reproducible mixing of the components of a first flow stream and a second flow stream. In some embodiments, the mixing of the first flow stream and the second flow stream occurs at a junction as depicted in FIG. 1. In some embodiments, the junction is a T-connector (also known as "Tee" connector) or a "Y" connector. In some embodiments, the junction is a T-connector. In some embodiments, the junction is a Y connector. In some embodiments, the T-connector has symmetrical arms, asymmetrical arms or arms comprising different diameters. In some embodiments, the T-connector has symmetrical arms. In some embodiments, the T-connector has asymmetrical arms. In some embodiments, the T-connector has arms comprising different diameters. In some embodiments, the Y-connector has symmetrical arms, asymmetrical arms or arms comprising different diameters. In some embodiments, the Y-connector has symmetrical arms. In some embodiments, the Y-connector has asymmetrical arms. In some embodiments, the Y-connector has arms comprising different diameters. In some embodiments, the flow rate and resultant mixing process is controlled by the diameter of one or more arms of the connector at the junction. In some embodiments, the diameter of an arm of the connector is controlled by a constriction placed over the arm. In some embodiments, the diameter of the connector arm is premade. In some embodiments, flow rate is controlled by a stopcock that is placed at one or more arms of the connector.

In some embodiments, a first conduit comprising a nucleic acid is connected at one arm of a T- or a Y-connector, and a second conduit comprising a lipid solution or LNP are connected at another arm of the T-connector or a Y-connector junction, thereby mixing the solutions from the first conduit and the second conduit at the T-connector or Y-connector junction. The mixing of the solutions results in the encapsulation of the nucleic acid in lipid nanoparticles.

In some embodiments, a first conduit comprising an mRNA is connected at one arm of a T- or a Y-connector, and a second conduit comprising a lipid solution or LNP are connected at another arm of the T-connector or a Y-connector junction, thereby mixing the solutions from the first conduit and the second conduit at the T-connector or Y-connector junction. The mixing of the solutions results in the encapsulation of the mRNA in lipid nanoparticles.

In some embodiments, a first conduit comprising a first lipid solution is connected at one arm of a T- or a Y-connector, and a second conduit comprising a second lipid solution is connected at another arm of the T-connector or a Y-connector junction, thereby mixing the solutions from the first conduit and the second conduit at the T-connector or Y-connector junction. The mixing of the solutions results in the production of liquid nanoparticles (LNPs). In some embodiments, the first lipid solution and the second lipid solution are the same. In some embodiments, the first lipid solution is a cationic lipid solution and the second lipid solution is a non-cationic (also referred to herein as "helper lipid") lipid solution. In some embodiments, the first lipid solution is a cationic lipid solution and the second lipid solution is a PEGylated lipid solution. In some embodiments, the first lipid solution is a non-cationic lipid solution and the second lipid solution is a PEGylated lipid solution. In some embodiments, the first lipid solution is a cationic lipid solution and the second lipid solution is a cholesterol-based lipid solution. In some embodiments, the first lipid solution is a cholesterol-based lipid solution and the second lipid solution is a non-cationic lipid solution. In some embodiments, the first lipid solution is a cholesterol-based lipid solution and the second lipid solution is a PEGylated lipid solution. In some embodiments, the lipid solution comprises pre-formed lipid nanoparticles. In some embodiments, the lipid solution comprises a suspension of pre-formed lipid nanoparticles.

In some embodiments, the first flow stream comprises an mRNA solution and the second flow stream comprises a lipid solution. In embodiments, the first flow stream comprises about between 50-99% water (e.g. 50, 55, 60, 65, 70, 75, 80, 85, 90, 95, 96, 97, 98, or 99% water). In some embodiments, the first flow stream comprises about 50% water. In some embodiments, the first flow stream comprises about 55% water. In some embodiments, the first flow stream comprises about 60% water. In some embodiments, the first flow stream comprises about 65% water. In some embodiments, the first flow stream comprises about 70% water. In some embodiments, the first flow stream comprises about 75% water. In some embodiments, the first flow stream comprises about 80% water. In some embodiments, the first flow stream comprises about 85% water. In some embodiments, the first flow stream comprises about 90% water. In some embodiments, the first flow stream comprises about 95% water. In some embodiments, the first flow stream comprises about 96% water. In some embodiments, the first flow stream comprises about 97% water. In some embodiments, the first flow stream comprises about 98% water. In some embodiments, the first flow stream comprises about 99% water.

In some embodiments, the second flow stream comprises about between 50-99% ethanol (e.g. 50, 55, 60, 65, 70, 75, 80, 85, 90, 95, 96, 97, 98, or 99% ethanol). In some embodiments, the second flow stream comprises about 50% ethanol. In some embodiments, the second flow stream comprises about 55% ethanol. In some embodiments, the second flow stream comprises about 60% ethanol. In some embodiments, the second flow stream comprises about 65% ethanol. In some embodiments, the second flow stream comprises about 70% ethanol. In some embodiments, the second flow stream comprises about 75% ethanol. In some embodiments, the second flow stream comprises about 80% ethanol. In some embodiments, the second flow stream comprises about 85% ethanol. In some embodiments, the second flow stream comprises about 90% ethanol. In some embodiments, the second flow stream comprises about 95% ethanol. In some embodiments, the second flow stream comprises about 96% ethanol. In some embodiments, the second flow stream comprises about 97% ethanol. In some embodiments, the second flow stream comprises about 98% ethanol. In some embodiments, the second flow stream comprises about 99% ethanol.

In some embodiments, the mixing of the first stream and the second stream results in a mixture comprising about 5-60% ethanol (e.g. about 5, 10, 15, 20, 25, 30, 35, 40, 45, 50, or 60% ethanol). In embodiments, the mixing of the first stream and the second stream results in a mixture comprising about 5% ethanol. In embodiments, the mixing of the first stream and the second stream results in a mixture comprising about 10% ethanol. In embodiments, the mixing of the first stream and the second stream results in a mixture comprising about 15% ethanol. In embodiments, the mixing of the first stream and the second stream results in a mixture comprising about 20% ethanol. In embodiments, the mixing of the first stream and the second stream results in a mixture comprising about 25% ethanol. In embodiments, the mixing of the first stream and the second stream results in a mixture comprising about 30% ethanol. In embodiments, the mixing of the first stream and the second stream results in a mixture comprising about 35% ethanol. In embodiments, the mixing of the first stream and the second stream results in a mixture comprising about 40% ethanol. In embodiments, the mixing of the first stream and the second stream results in a mixture comprising about 45% ethanol. In embodiments, the mixing of the first stream and the second stream results in a mixture comprising about 50% ethanol. In embodiments, the mixing of the first stream and the second stream results in a mixture comprising about 55% ethanol. In embodiments, the mixing of the first stream and the second stream results in a mixture comprising about 60% ethanol.

The process described herein results in reproducible, high nucleic acid encapsulation efficiencies. In some embodiments, using the process described herein mRNA is encapsulated in lipids at an efficiency of about between 60-100% (e.g. about 75, 76, 77, 78, 79, 80, 81, 82, 83, 84, 85, 86, 87, 88, 89, 90, 91, 92, 93, 94, 95, 98, or 99% encapsulation efficiency). In some embodiments, mRNA is encapsulated in lipids at an efficiency of about 60%. In some embodiments, mRNA is encapsulated in lipids at an efficiency of about 65%. In some embodiments, mRNA is encapsulated in lipids at an efficiency of about 70%. In some embodiments, mRNA is encapsulated in lipids at an efficiency of about 75%. In some embodiments, mRNA is encapsulated in lipids at an efficiency of about 76%. In some embodiments, mRNA is encapsulated in lipids at an efficiency of about 77%. In some embodiments, mRNA is encapsulated in lipids at an efficiency of about 78%. In some embodiments, mRNA is encapsulated in lipids at an efficiency of about 79%. In some embodiments, mRNA is encapsulated in lipids at an efficiency of about 80%. In some embodiments, mRNA is encapsulated in lipids at an efficiency of about 81%. In some embodiments, mRNA is encapsulated in lipids at an efficiency of about 82%. In some embodiments, mRNA is encapsulated in lipids at an efficiency of about 83%. In some embodiments, mRNA is encapsulated in lipids at an efficiency of about 84%. In some embodiments, mRNA is encapsulated in lipids at an efficiency of about 85%. In some embodiments, mRNA is encapsulated in lipids at an efficiency of about 86%. In some embodiments, mRNA is encapsulated in lipids at an efficiency of about 87%. In some embodiments, mRNA is encapsulated in lipids at an efficiency of about 88%. In some embodiments, mRNA is encapsulated in lipids at an efficiency of about 89%. In some embodiments, mRNA is encapsulated in lipids at an efficiency of about 90%. In some embodiments, mRNA is encapsulated in lipids at an efficiency of about 91%. In some embodiments, mRNA is encapsulated in lipids at an efficiency of about 92%. In some embodiments, mRNA is encapsulated in lipids at an efficiency of about 93%. In some embodiments, mRNA is encapsulated in lipids at an efficiency of about 94%. In some embodiments, mRNA is encapsulated in lipids at an efficiency of about 95%.

The encapsulated nucleic acids using the process described herein have a nanoparticle size of about 40-150 nm. In some embodiments, the encapsulation efficiency is about 60%. In some embodiments, the encapsulation efficiency is about 65%. In some embodiments, the encapsulation efficiency is about 70%. In some embodiments, the encapsulation efficiency is about 75%. In some embodiments, the encapsulation efficiency is about 80%. In some embodiments, the encapsulation efficiency is about 85%. In some embodiments, the encapsulation efficiency is about 90%. In some embodiments, the encapsulation efficiency is about 95%. In some embodiments, the encapsulation efficiency is about 96%. In some embodiments, the encapsulation efficiency is about 97%. In some embodiments, the encapsulation efficiency is about 98%. In some embodiments, the encapsulation efficiency is about 99%.

The process described herein has high amounts of mRNA recovery. In embodiments, the process results in at least about 50, 55, 60, 65, 70, 75, 80, 85, 90, 95, 96, 97, 98, or 99% recovery of mRNA. In embodiments, the process results in at least about 50% recover of mRNA. In embodiments, the process results in at least about 55% recover of mRNA. In embodiments, the process results in at least about 60% recover of mRNA. In embodiments, the process results in at least about 65% recover of mRNA. In embodiments, the process results in at least about 70% recover of mRNA. In embodiments, the process results in at least about 75% recover of mRNA. In embodiments, the process results in at least about 80% recover of mRNA. In embodiments, the process results in at least about 85% recover of mRNA. In embodiments, the process results in at least about 90% recover of mRNA. In embodiments, the process results in at least about 95% recover of mRNA. In embodiments, the process results in at least about 96% recover of mRNA. In embodiments, the process results in at least about 97% recover of mRNA. In embodiments, the process results in at least about 98% recover of mRNA. In embodiments, the process results in at least about 99% recover of mRNA.

In some embodiments, the process results in at least about 0.1 mg, 0.5 mg, 1 mg, 5 mg, 10 mg, 100 mg, 500 mg, or 1,000 mg of encapsulated mRNA. In some embodiments, the process results in at least about 0.1 mg of encapsulated mRNA. In some embodiments, the process results in at least about 0.5 mg of encapsulated mRNA. In some embodiments, the process results in at least about 1 mg of encapsulated mRNA. In some embodiments, the process results in at least about 5 mg of encapsulated mRNA. In some embodiments, the process results in at least about 10 mg of encapsulated mRNA. In some embodiments, the process results in at least about 100 mg of encapsulated mRNA. In some embodiments, the process results in at least about 500 mg of encapsulated mRNA. In some embodiments, the process results in at least about 1000 mg of encapsulated mRNA.

In some embodiments, the mixing of the first and the second streams occurs simultaneously. In some embodiments, the mixing of the first and second streams occurs asynchronously.

In some embodiments, the use of the process disclosed herein results in lipid nanoparticles that do not require further purification.

High Throughput Formulation

Figure 7:
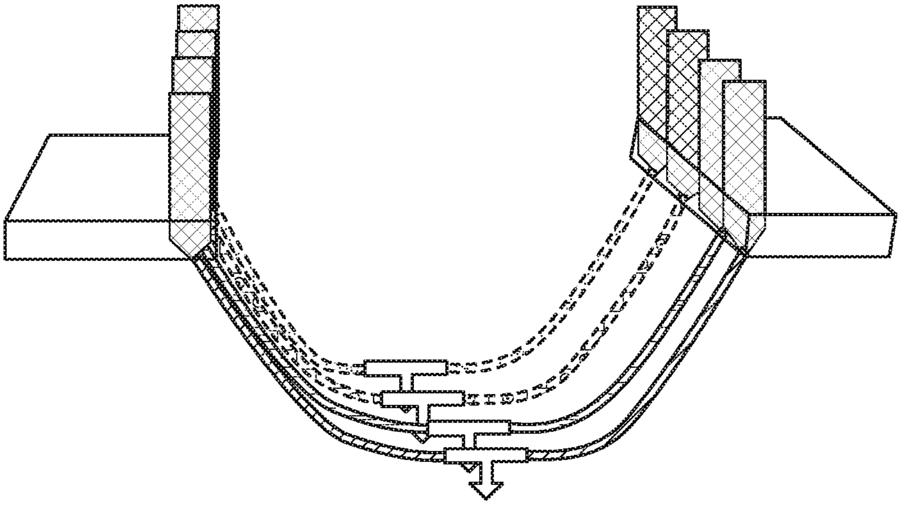
FIG. 7 depicts a schematic of a tandem process in which liquids are added to pairs of reservoirs at the same time, followed by the addition of liquids the next pairs of reservoirs in succession
Figure 8:
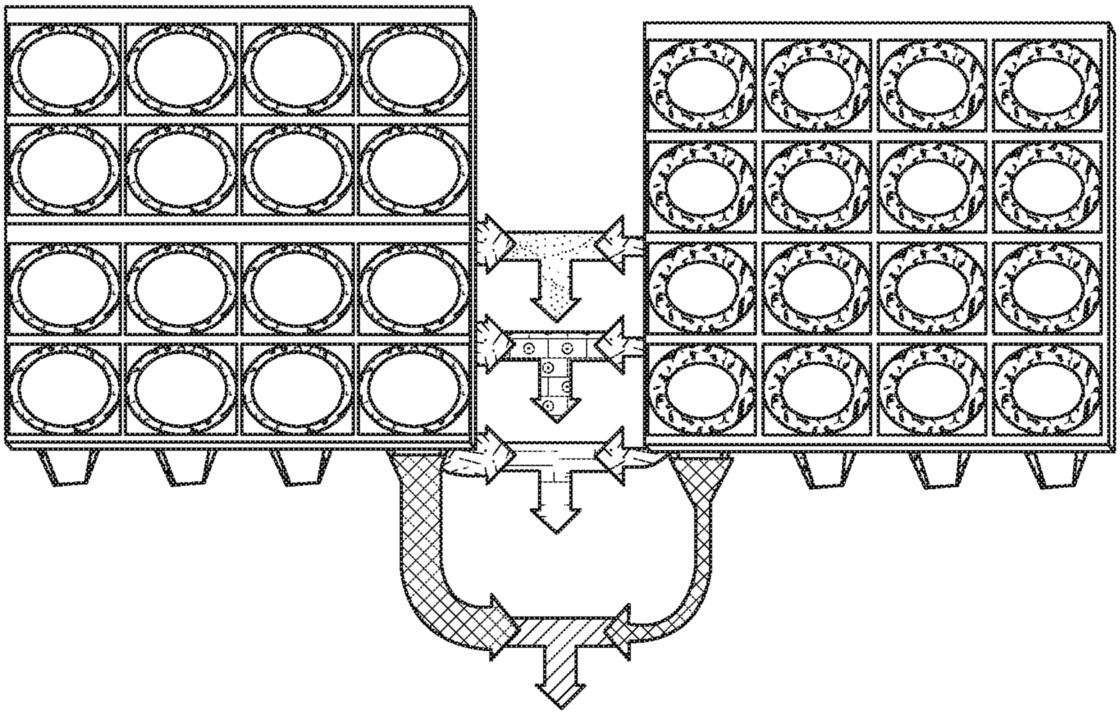
FIG. 8 depicts a schematic of a high throughput process in which multiple pairs of conduits are used.

The gravity-based encapsulation process is configurable such that multiple flow streams are envisioned. Multiple flow streams allows for a high throughput process. In embodiments, an assembly line approach is achieved wherein liquids are added to pairs of reservoirs at the same time, followed by the addition of liquids to the next pairs of reservoirs in succession. An embodiment of the gravity-based encapsulation process which depicts multiple streams is shown in FIG. 7 and FIG. 8. In some embodiments, multiple pairs of first conduit streams (Flow 1) and second conduit streams (Flow 2) are used. For example, in some embodiments the process comprises at least about 1 pair, 5 pairs, 10 pairs, 20 pairs, 30 pairs, 40 pairs, 50 pairs, 100 pairs, 150 pairs, 200 pairs, 250 pairs, or 300 pairs of first conduit streams and second conduit streams. In some embodiments, the process comprises 1 pair of first conduit streams and second conduit streams. In some embodiments, the process comprises about 5 pairs of first conduit streams and second conduit streams. In some embodiments, the process comprises about 10 pairs of first conduit streams and second conduit streams. In some embodiments, the process comprises about 20 pairs of first conduit streams and second conduit streams. In some embodiments, the process comprises about 30 pairs of first conduit streams and second conduit streams. In some embodiments, the process comprises about 40 pairs of first conduit streams and second conduit streams. In some embodiments, the process comprises about 50 pairs of first conduit streams and second conduit streams. In some embodiments, the process comprises about 100 pairs of first conduit streams and second conduit streams. In some embodiments, the process comprises about 150 pairs of first conduit streams and second conduit streams. In some embodiments, the process comprises about 200 pairs of first conduit streams and second conduit streams. In some embodiments, the process comprises about 250 pairs of first conduit streams and second conduit streams. In some embodiments, the process comprises about 300 pairs of first conduit streams and second conduit streams.

In some embodiments, each individual first stream provides a different nucleic acid solution. In some embodiments, each individual first stream provides the same nucleic acid. In some embodiments, each individual first stream provides a different mRNA solution. In some embodiments, each individual first stream provides the same mRNA solution. In some embodiments, each individual second stream provides a different lipid solution. In some embodiments, each individual second stream provide the same lipid solution.

Messenger (mRNA)

The gravity-based encapsulation process described herein can be used with any kind of nucleic acid. In some embodiments, the nucleic acid is an RNA, including for example, messenger RNA (mRNA), antisense RNA (aRNA), small interfering RNA (siRNA), CRISPR RNA (crRNA), long noncoding RNA (lncRNA), microRNA (miRNA), Piwi-interacting RNA (piRNA), short hairpin RNA (shRNA), trnas-acting siRNA (tasiRNA), repeat associated siRNA (rasiRNA), 7SK RNA (7SK), enhancer RNA (eRNA), ribosomal RNA (rRNA), signal recognition particle RNA (SRP RNA), transfer RNA (tRNA), small nuclear RNA (snRNA), small nucleolar RNA (snoRNA), SmY RNA (SmY), small Cajal body-specific RNA (scaRNA), and guide RNA (gRNA). In embodiments, the RNA is mRNA.

The present invention may be used to encapsulate any mRNA. mRNA is typically thought of as the type of RNA that carries information from DNA to the ribosome. The existence of mRNA is typically very brief and includes processing and translation, followed by degradation. Typically, in eukaryotic organisms, mRNA processing comprises the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this “tail” serves to protect the mRNA from exonuclease degradation. Messenger RNA is translated by the ribosomes into a series of amino acids that make up a protein.

mRNAs may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, in vitro synthesized mRNA may be purified before formulation and encapsulation to remove undesirable impurities including various enzymes and other reagents used during mRNA synthesis.

The present invention may be used to formulate and encapsulate mRNAs of a variety of lengths. In some embodiments, the present invention may be used to formulate and encapsulate in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to formulate and encapsulate in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

The present invention may be used to formulate and encapsulate mRNA that is unmodified or mRNA containing one or more modifications that typically enhance stability. In some embodiments, modifications are selected from modified nucleotide, modified sugar phosphate backbones, 5' and/or 3' untranslated region.

In some embodiments, modifications of mRNA may include modifications of the nucleotides of the RNA. A modified mRNA according to the invention can include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

Typically, mRNA synthesis includes the addition of a “cap” on the N-terminal (5') end, and a “tail” on the C-terminal (3') end. The presence of the cap is important in providing resistance to nucleases found in most eukaryotic cells. The presence of a “tail” serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. 2'-O-methylation may also occur at the first base and/or second base following the 7-methyl guanosine triphosphate residues. Examples of cap structures include, but are not limited to, m7GpppNp-RNA, m7GpppNmp-RNA and m7GpppNmpNmp-RNA (where m indicates 2'-Omethyl residues).

In some embodiments, mRNAs include a 5' and/or 3' untranslated region. In some embodiments, a 5' untranslated region includes one or more elements that affect an mRNA’s stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect a mRNA’s stability of location in a cell, or one or more binding sites for miRNAs. In some embodiments, a 3' untranslated region may be between 50 and 500 nucleotides in length or longer.

While mRNA provided from in vitro transcription reactions may be desirable in some embodiments, other sources of mRNA are contemplated as within the scope of the invention including mRNA produced from bacteria, fungi, plants, and/or animals.

In some embodiments, the mRNA used in the process described herein is unmodified. In some embodiments, the mRNA used in the process disclosed herein is modified. In some embodiments, the mRNA used in the process described herein is codon-optimized.

The present invention may be used to formulate and encapsulate mRNAs encoding a variety of proteins.

mRNA Solution mRNA may be provided in a solution to be mixed with a lipid solution such that the mRNA may be encapsulated in lipid nanoparticles. A suitable mRNA solution may be any aqueous solution containing mRNA to be encapsulated at various concentrations. For example, a suitable mRNA solution may contain a mRNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable mRNA solution may contain a mRNA at a concentration ranging from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml. In some embodiments, a suitable mRNA solution may contain an mRNA at a concentration up to about 5.0 mg/ml, 4.0 mg/ml, 3.0 mg/ml, 2.0 mg/ml, 1.0 mg/ml, 0.09 mg/ml, 0.08 mg/ml, 0.07 mg/ml, 0.06 mg/ml, or 0.05 mg/ml.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate. In some embodiments, suitable concentration of the buffering agent may range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM. In some embodiments, suitable concentration of the buffering agent is or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM.

Exemplary salts can include sodium chloride, magnesium chloride, and potassium chloride. In some embodiments, suitable concentration of salts in a mRNA solution may range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM. Salt concentration in a suitable mRNA solution is or greater than about 1 mM, 5 mM, 10 mM, 20 mM, 30 mM, 40 mM, 50 mM, 60 mM, 70 mM, 80 mM, 90 mM, or 100 mM.

In some embodiments, a suitable mRNA solution may have a pH ranging from about 3.5-6.5, 3.5-6.0, 3.5-5.5., 3.5-5.0, 3.5-4.5, 4.0-5.5, 4.0-5.0, 4.0-4.9, 4.0-4.8, 4.0-4.7, 4.0-4.6, or 4.0-4.5. In some embodiments, a suitable mRNA solution may have a pH of or no greater than about 3.5, 4.0, 4.1, 4.2, 4.3, 4.4, 4.5, 4.6, 4.7, 4.8, 4.9, 5.0, 5.2, 5.4, 5.6, 5.8, 6.0, 6.1, 6.3, and 6.5.

Various methods may be used to prepare an mRNA solution suitable for the present invention. In some embodiments, mRNA may be directly dissolved in a buffering solution described herein. In some embodiments, an mRNA solution may be generated by mixing an mRNA stock solution with a buffering solution prior to mixing with a lipid solution for encapsulation. In some embodiments, an mRNA solution may be generated by mixing an mRNA stock solution with a buffering solution immediately before mixing with a lipid solution for encapsulation. In some embodiments, a suitable mRNA stock solution may contain mRNA in water at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

In some embodiments, an mRNA stock solution is mixed with a buffering solution using a pump. Exemplary pumps include but are not limited to gear pumps, peristaltic pumps and centrifugal pumps.

Typically, the buffering solution is mixed at a rate greater than that of the mRNA stock solution. For example, the buffering solution may be mixed at a rate at least 1×, 2×, 3×, 4×, 5×, 6×, 7×, 8×, 9×, 10×, 15×, or 20× greater than the rate of the mRNA stock solution. In some embodiments, a buffering solution is mixed at a flow rate ranging between about 100-6000 ml/minute (e.g., about 100-300 ml/minute, 300-600 ml/minute, 600-1200 ml/minute, 1200-2400 ml/minute, 2400-3600 ml/minute, 3600-4800 ml/minute, 4800-6000 ml/minute, or 60-420 ml/minute). In some embodiments, a buffering solution is mixed at a flow rate of or greater than about 60 ml/minute, 100 ml/minute, 140 ml/minute, 180 ml/minute, 220 ml/minute, 260 ml/minute, 300 ml/minute, 340 ml/minute, 380 ml/minute, 420 ml/minute, 480 ml/minute, 540 ml/minute, 600 ml/minute, 1200 ml/minute, 2400 ml/minute, 3600 ml/minute, 4800 ml/minute, or 6000 ml/minute.

In some embodiments, a mRNA stock solution is mixed at a flow rate ranging between about 10-600 ml/minute (e.g., about 5-50 ml/minute, about 10-30 ml/minute, about 30-60 ml/minute, about 60-120 ml/minute, about 120-240 ml/minute, about 240-360 ml/minute, about 360-480 ml/minute, or about 480-600 ml/minute). In some embodiments, a mRNA stock solution is mixed at a flow rate of or greater than about 5 ml/minute, 10 ml/minute, 15 ml/minute, 20 ml/minute, 25 ml/minute, 30 ml/minute, 35 ml/minute, 40 ml/minute, 45 ml/minute, 50 ml/minute, 60 ml/minute, 80 ml/minute, 100 ml/minute, 200 ml/minute, 300 ml/minute, 400 ml/minute, 500 ml/minute, or 600 ml/minute.

Lipid Solution

According to the present invention, a lipid solution contains a mixture of lipids suitable to form lipid nanoparticles for encapsulation of mRNA. In some embodiments, a suitable lipid solution is ethanol based. For example, a suitable lipid solution may contain a mixture of desired lipids dissolved in pure ethanol (i.e., 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. For example, a suitable lipid solution may contain a mixture of desired lipids at a total concentration of or greater than about 0.1 mg/ml, 0.5 mg/ml, 1.0 mg/ml, 2.0 mg/ml, 3.0 mg/ml, 4.0 mg/ml, 5.0 mg/ml, 6.0 mg/ml, 7.0 mg/ml, 8.0 mg/ml, 9.0 mg/ml, 10 mg/ml, 15 mg/ml, 20 mg/ml, 30 mg/ml, 40 mg/ml, 50 mg/ml, or 100 mg/ml. In some embodiments, a suitable lipid solution may contain a mixture of desired lipids at a total concentration ranging from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml. In some embodiments, a suitable lipid solution may contain a mixture of desired lipids at a total concentration up to about 100 mg/ml, 90 mg/ml, 80 mg/ml, 70 mg/ml, 60 mg/ml, 50 mg/ml, 40 mg/ml, 30 mg/ml, 20 mg/ml, or 10 mg/ml.

Any desired lipids may be mixed at any ratios suitable for encapsulating mRNAs. In some embodiments, a suitable lipid solution contain a mixture of desired lipids including cationic lipids, helper lipids (e.g. non cationic lipids and/or cholesterol lipids) and/or PEGylated lipids. In some embodiments, a suitable lipid solution contain a mixture of desired lipids including one or more cationic lipids, one or more helper lipids (e.g. non cationic lipids and/or cholesterol lipids) and one or more PEGylated lipids.

In some embodiments, the lipid solution used in the process includes one or more cationic lipids, one or more helper lipids, and one or more PEG-modified lipids. In some embodiments, the lipid solution includes one or more cationic lipids. In some embodiments, the lipid solution includes one or more helper lipids. In some embodiments, the lipid solution includes one or more PEG-modified lipids.

In some embodiments, the lipid solution includes one or more cationic lipids and one or more helper lipids. In some embodiments, the lipid solution includes one or more cationic lipids and one or more PEG-modified lipids. In some embodiments, the lipid solution includes one or more helper lipids and one or more PEG-modified lipids.

Cationic Lipids

As used herein, the phrase "cationic lipids" refers to any of a number of lipid species that have a net positive charge at a selected pH, such as physiological pH.

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

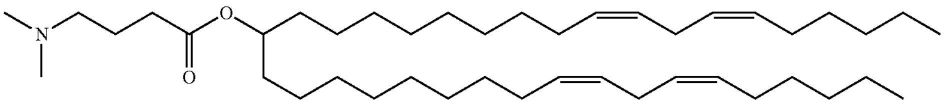 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

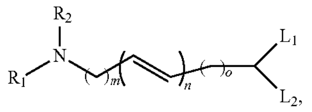

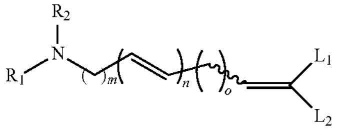

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z,18Z)—N,N-dimethyl-6-(9Z,12Z)-octadeca-9,12-dien-1-yl) tetracosa-15,18-dien-1-amine ("HGT5000"), having a compound structure of:

(HGT-5000)

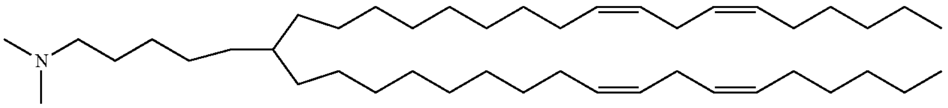

and pharmaceutically acceptable salts thereof. In certain embodiments, the compositions and methods of the present invention include the cationic lipid (15Z,18Z)—N,N-dimethyl-6-((9Z,12Z)-octadeca-9,12-dien-1-yl) tetracosa-4,15,18-trien-1-amine ("HGT5001"), having a compound structure of:

(HGT-5001)

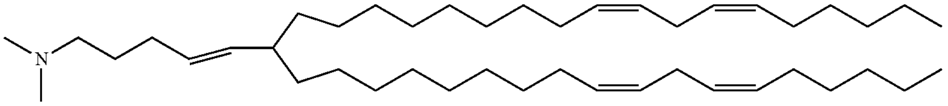

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5, 15,18-trien-1-amine ("HGT5002"), having a compound structure of:

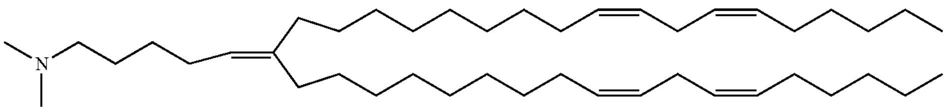

(HGT-5002)

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

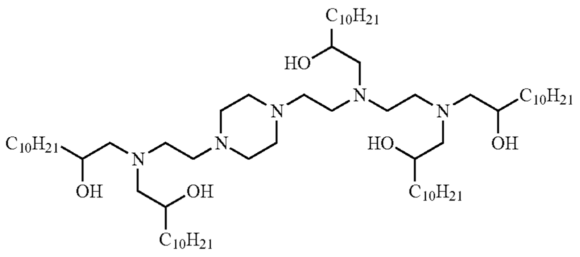

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

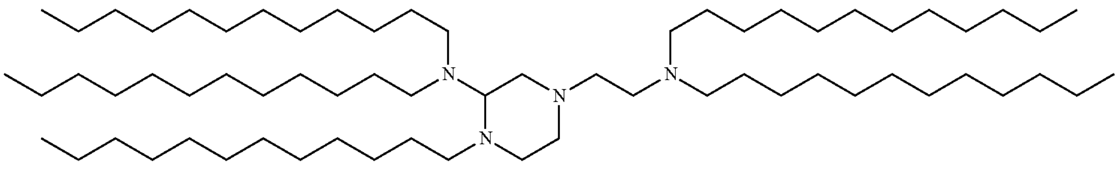 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

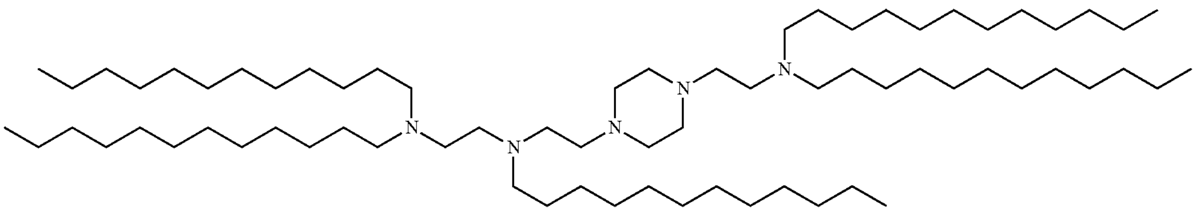 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

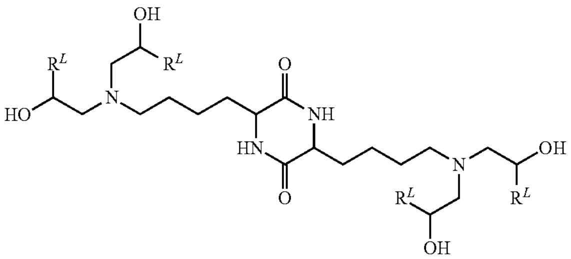

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

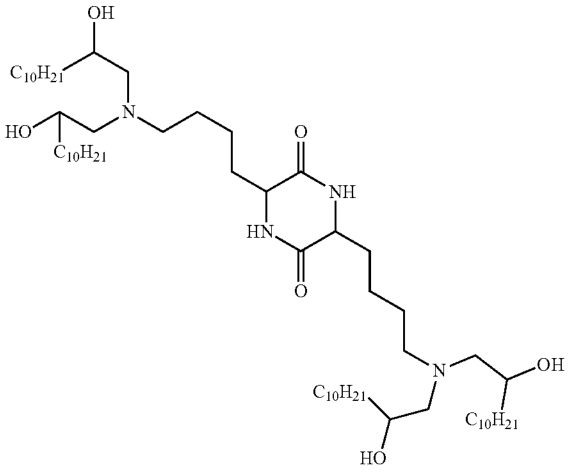

and pharmaceutically acceptable salts thereof. In certain embodiments, the compositions and methods of the present invention include a cationic lipid having a compound structure of:

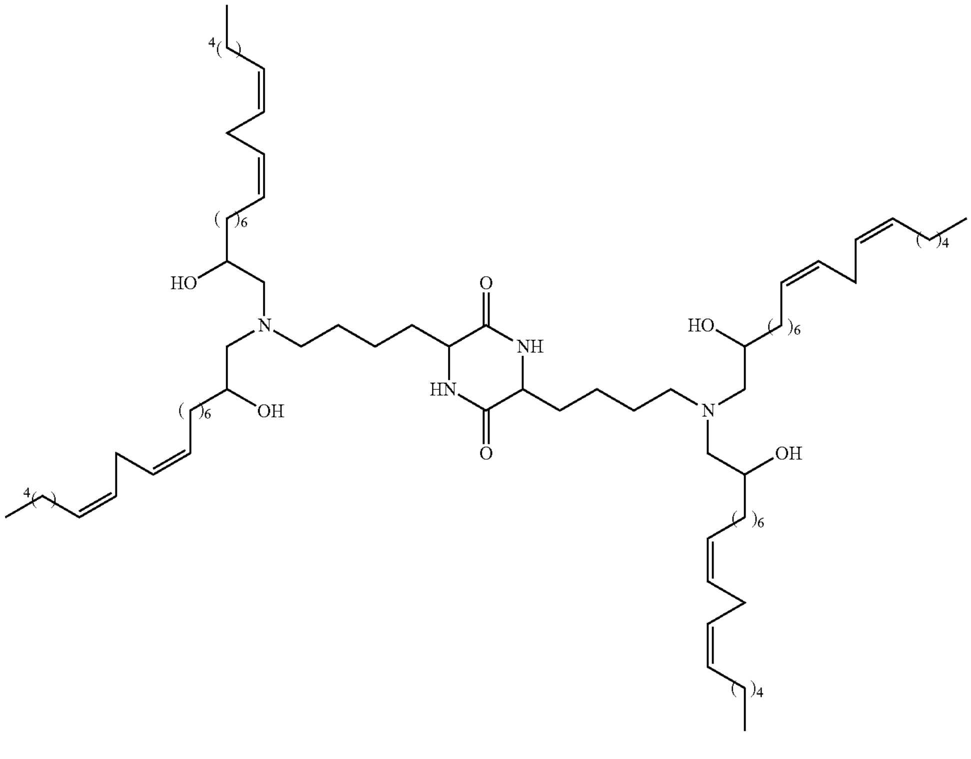

and pharmaceutically acceptable salts thereof. In certain embodiments, the compositions and methods of the present invention include a cationic lipid having a compound structure of:

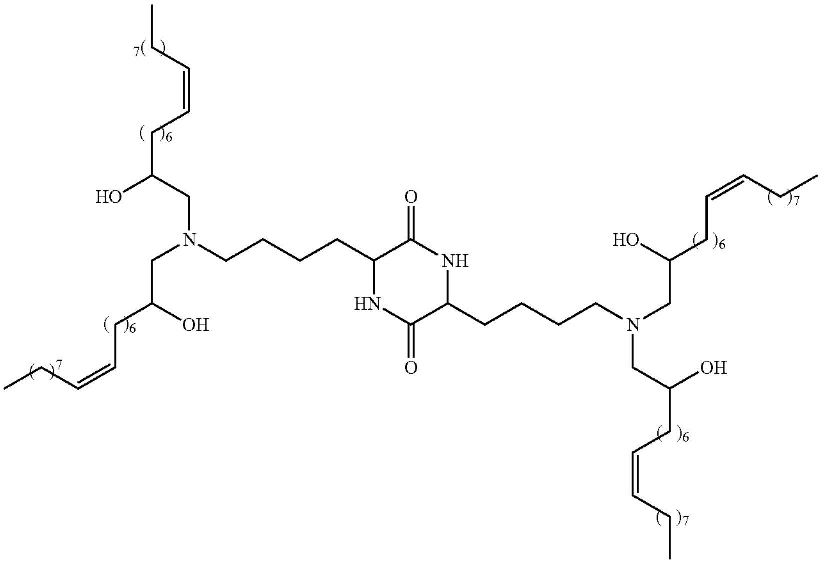

and pharmaceutically acceptable salts thereof. In certain embodiments, the compositions and methods of the present invention include a cationic lipid having a compound structure of:

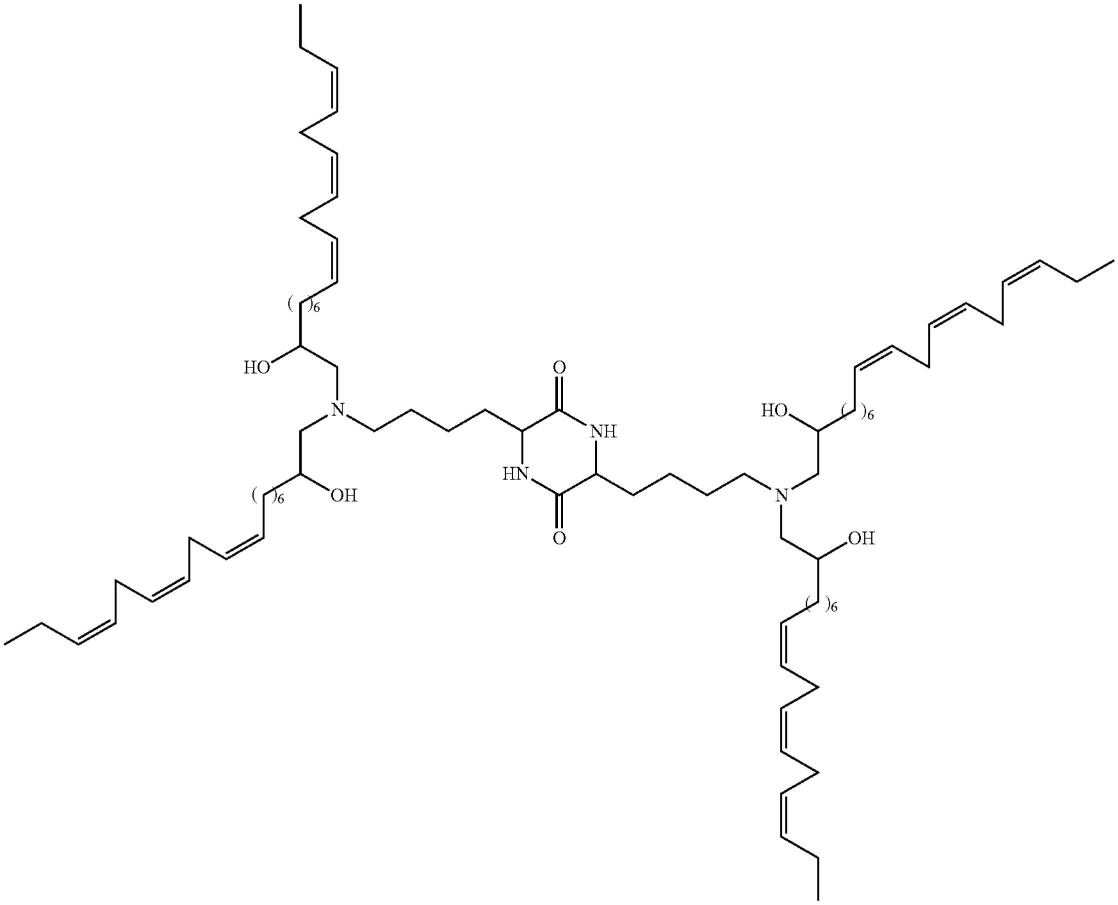

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

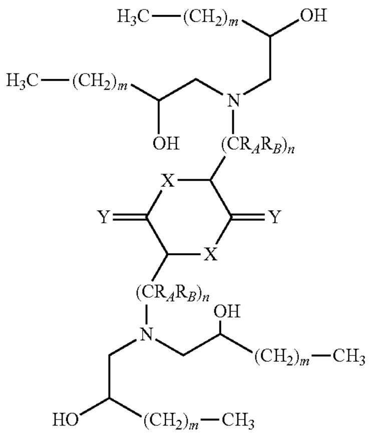

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

(Target 23)

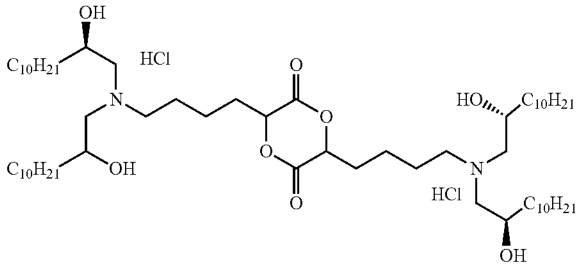

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

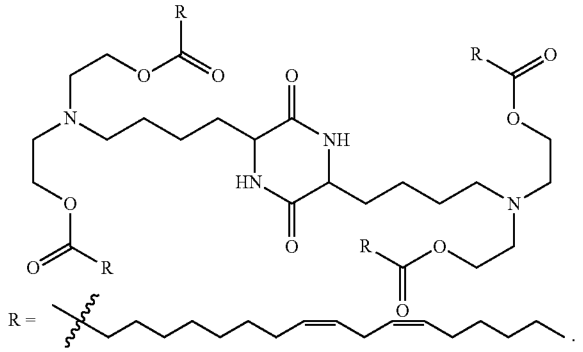

or a pharmaceutically acceptable salt thereof. In some embodiments, the compositions and methods of the present invention include a cationic lipid having the compound structure:

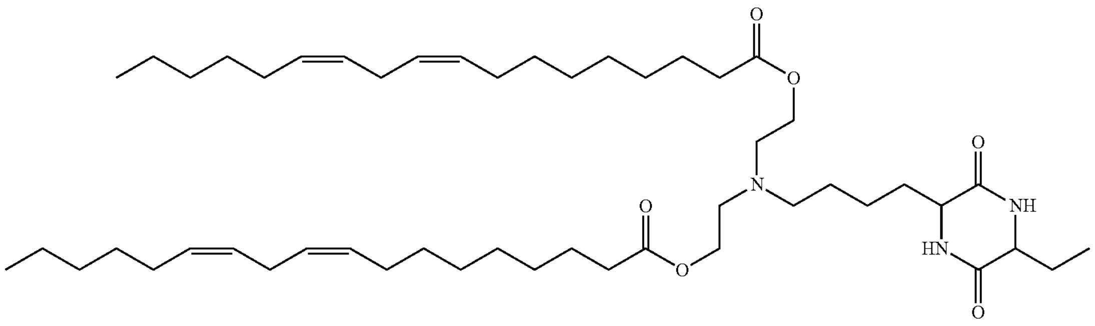 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

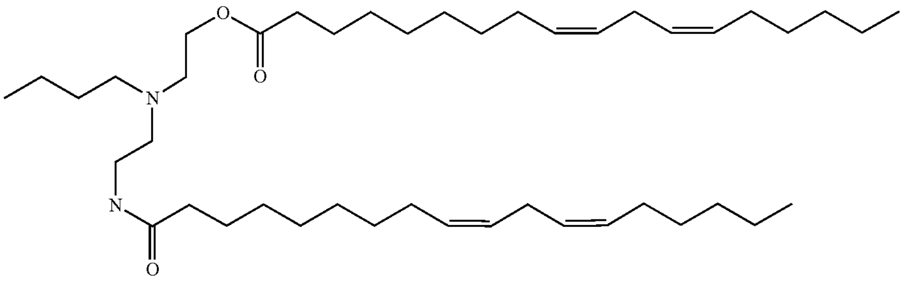 [SMILES: CCCCC/C=C\C/C=C\CCCCCCCC(=O)NCCN(CCCC)CCOC(=O)CCCCCCC/C=C\C/C=C\CCCCC]

or a pharmaceutically acceptable salt thereof.

Other suitable cationic lipids for use in the compositions and methods of the present invention include cationic lipids as described in U.S. Provisional Patent Application Ser. No. 62/758,179, which is incorporated herein by reference. In some embodiments, the compositions and methods of the present invention include a cationic lipid of the following formula:

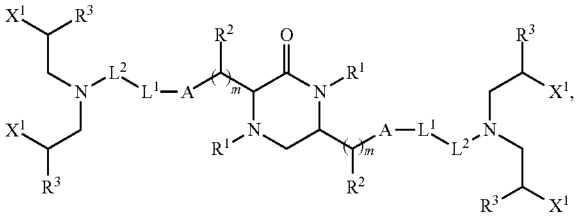

or a pharmaceutically acceptable salt thereof, wherein each $R^1$ and $R^2$ is independently H or $C_1$-$C_6$ aliphatic; each m is independently an integer having a value of 1 to 4; each A is independently a covalent bond or arylene; each $L^1$ is independently an ester, thioester, disulfide, or anhydride group; each $L^2$ is independently $C_2$-$C_{10}$ aliphatic; each $X^1$ is independently H or OH; and each $R^3$ is independently $C_6$-$C_{20}$ aliphatic. In some embodiments, the compositions and methods of the present invention include a cationic lipid of the following formula:

(Compound 1)

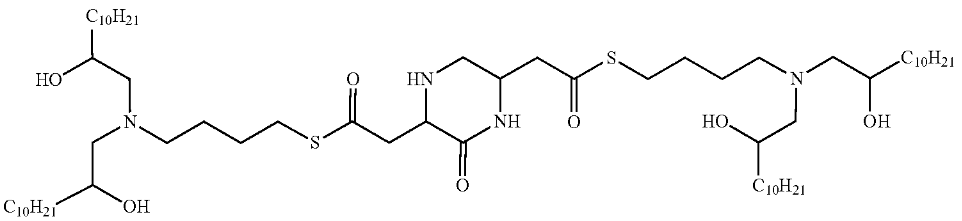

or a pharmaceutically acceptable salt thereof. In some embodiments, the compositions and methods of the present invention include a cationic lipid of the following formula:

(Compound 2)

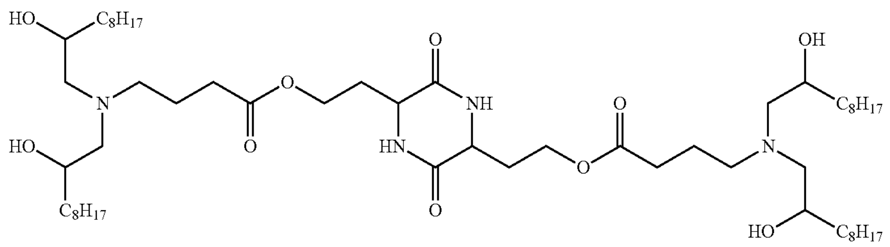

or a pharmaceutically acceptable salt thereof. In some embodiments, the compositions and methods of the present invention include a cationic lipid of the following formula:

(Compound 3)

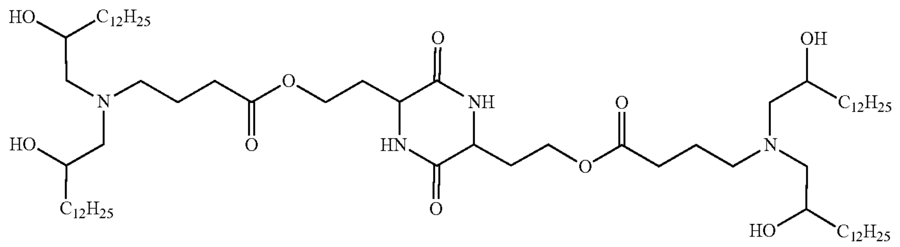

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

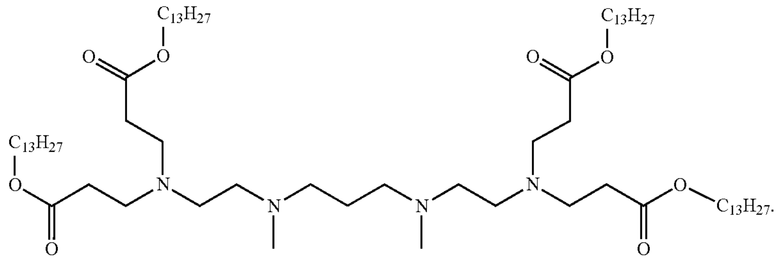

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

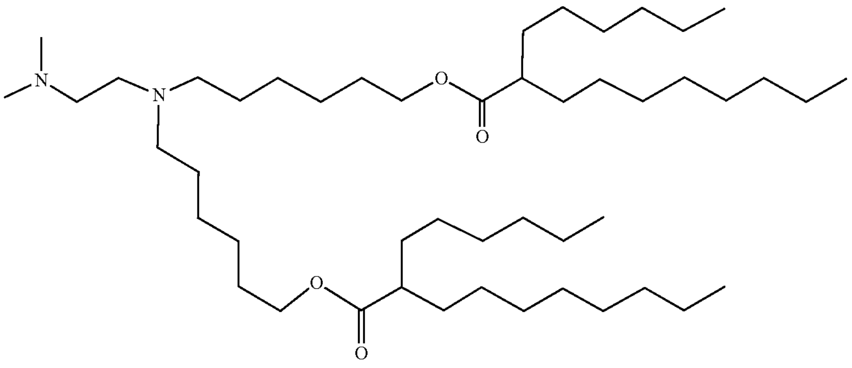 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

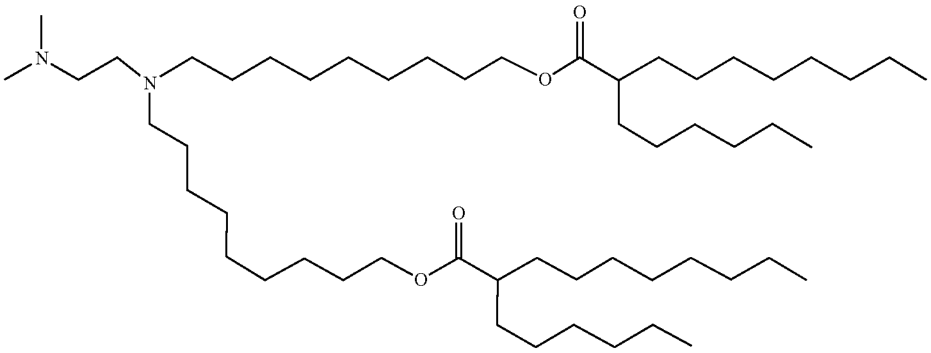

and pharmaceutically acceptable salts thereof. In some embodiments, the compositions and methods of the present invention include a cationic lipid having the compound structure:

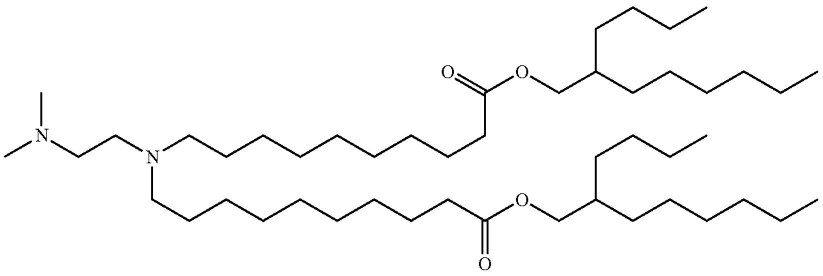 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

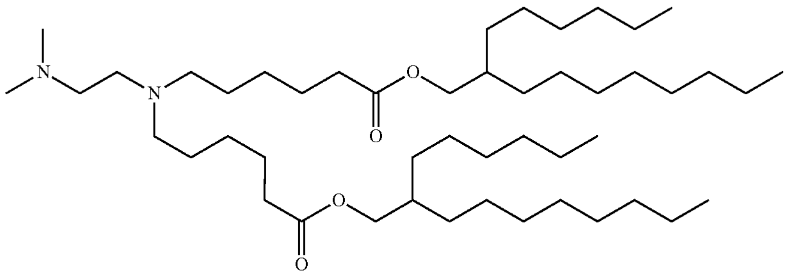 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

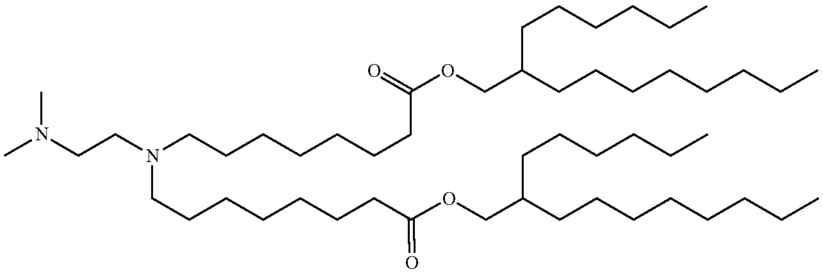 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

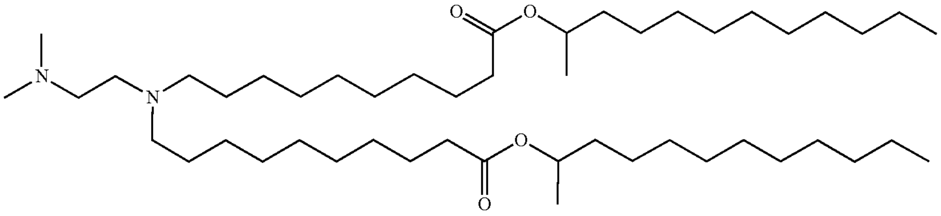

and pharmaceutically acceptable salts thereof. In some embodiments, the compositions and methods of the present invention include a cationic lipid having the compound structure:

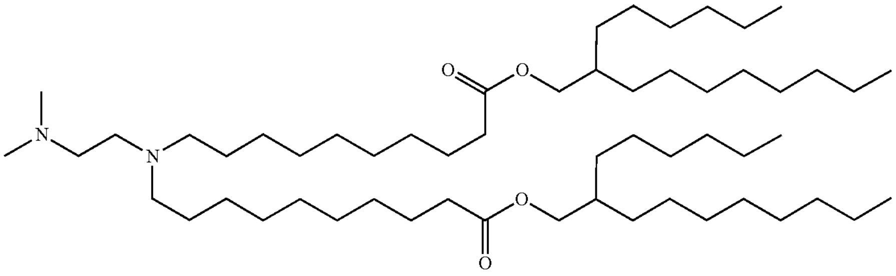 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

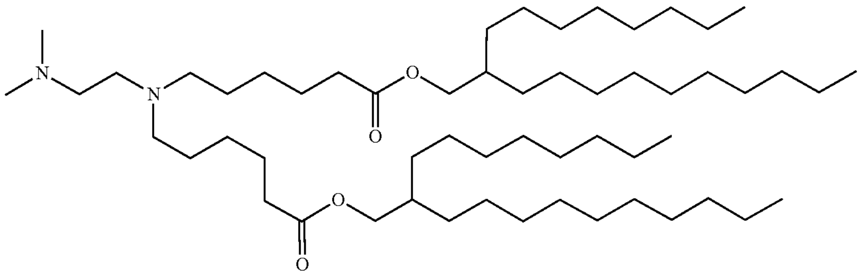 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

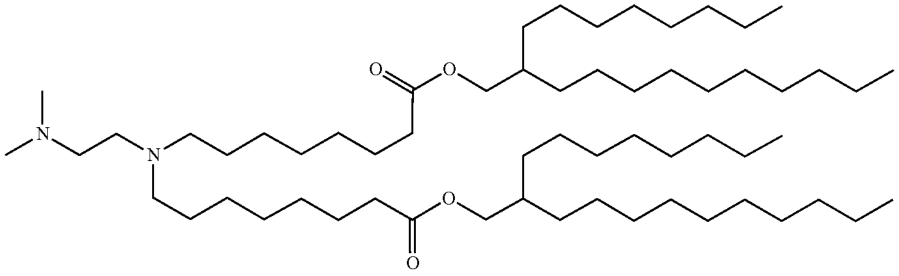 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

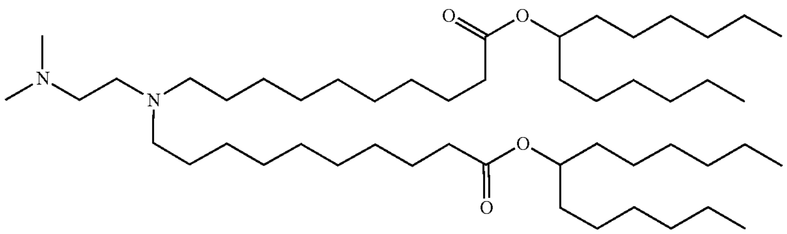

and pharmaceutically acceptable salts thereof. In some embodiments, the compositions and methods of the present invention include a cationic lipid having the compound structure:

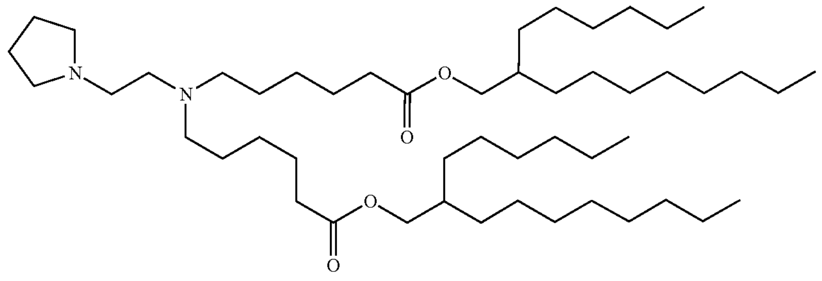 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

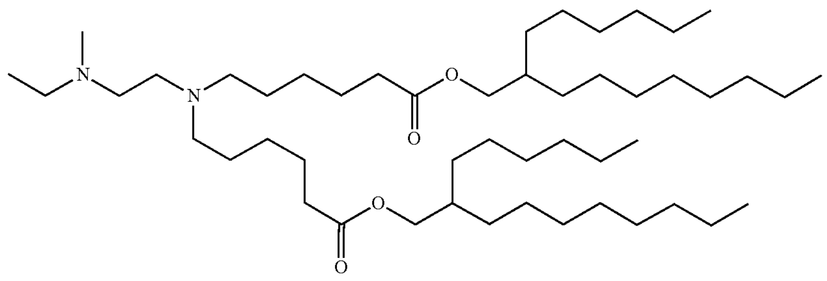 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

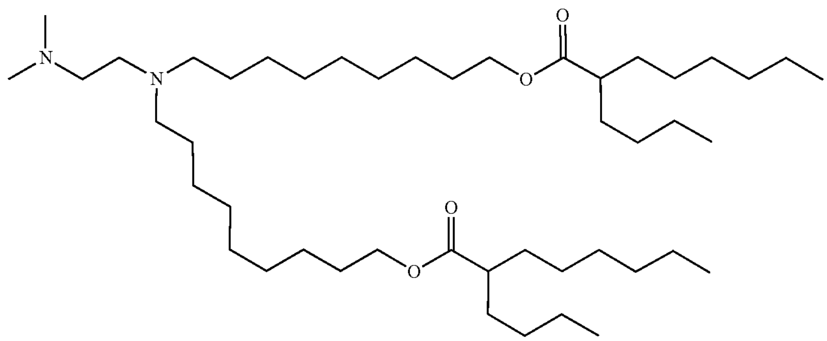 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

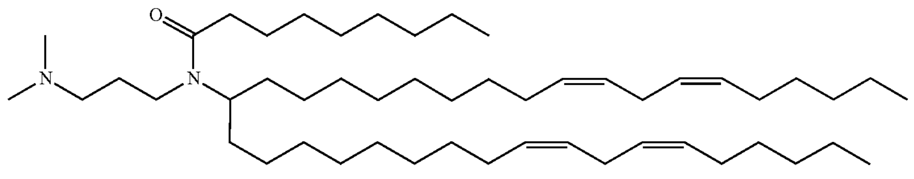 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

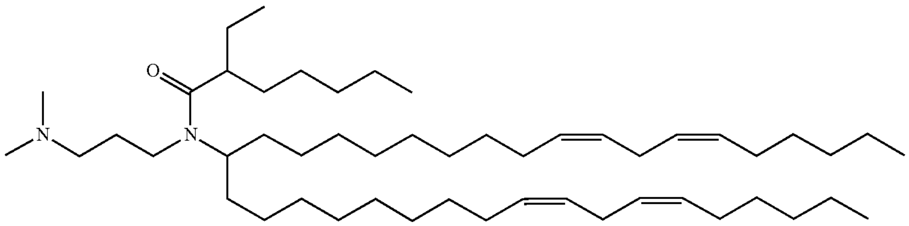 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

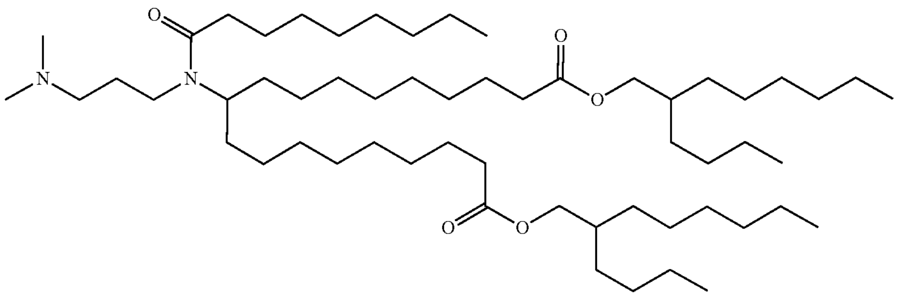 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

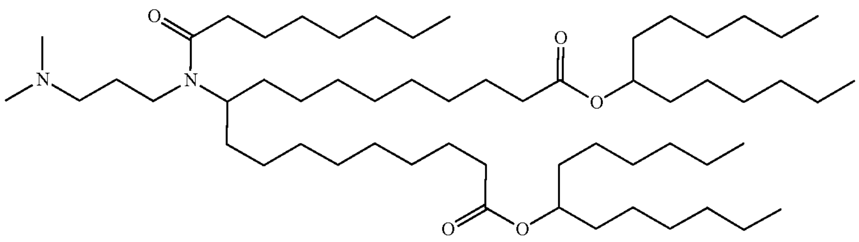 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

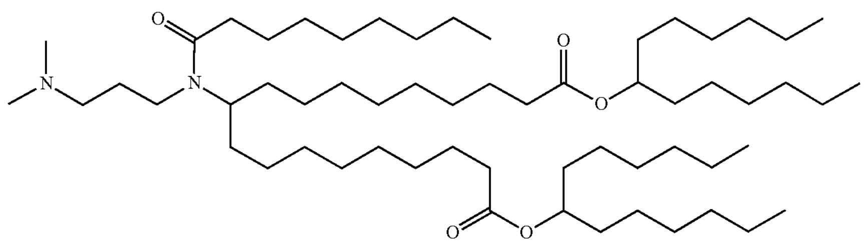 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

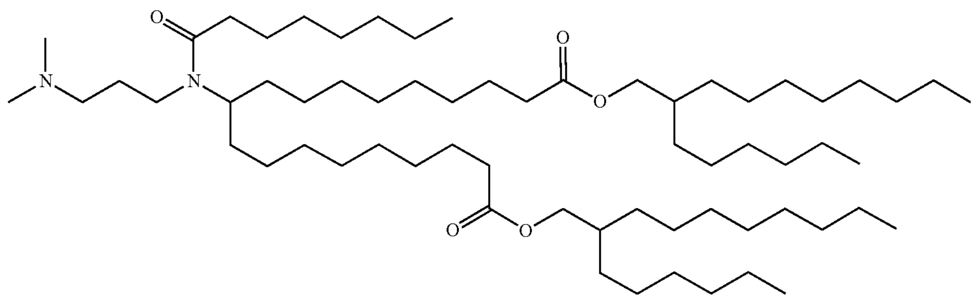 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

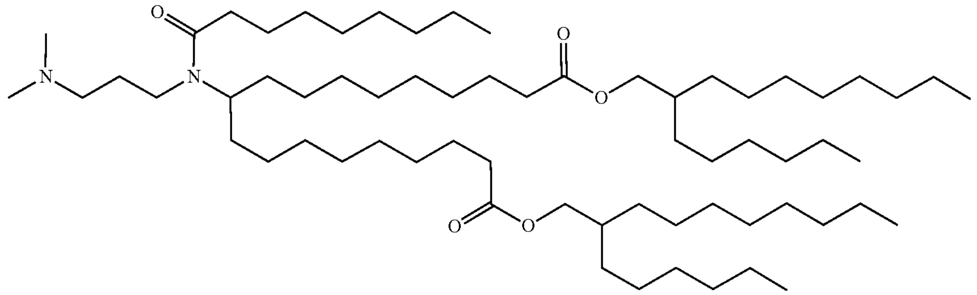 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

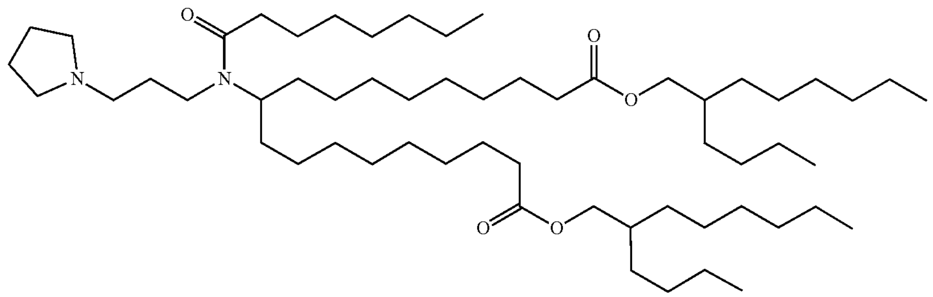 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

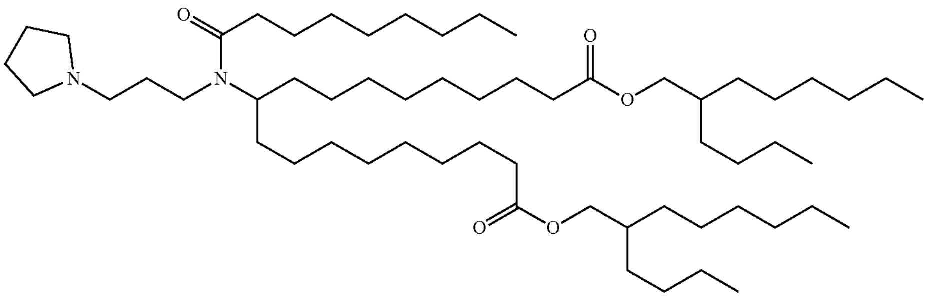 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

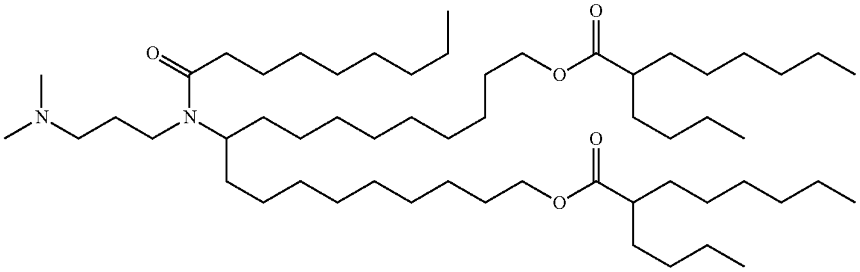 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

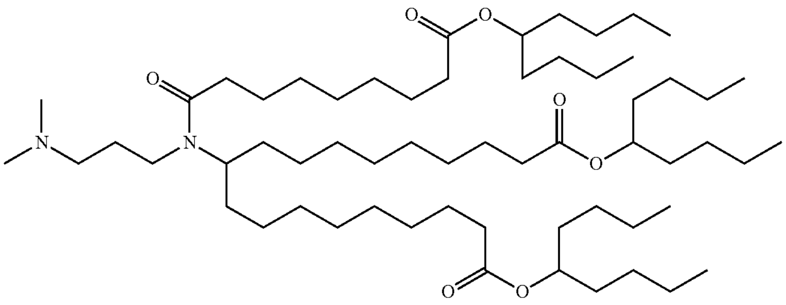 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

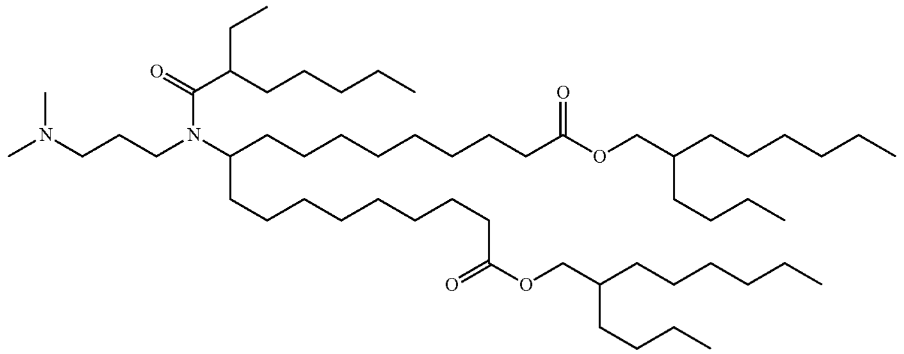 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

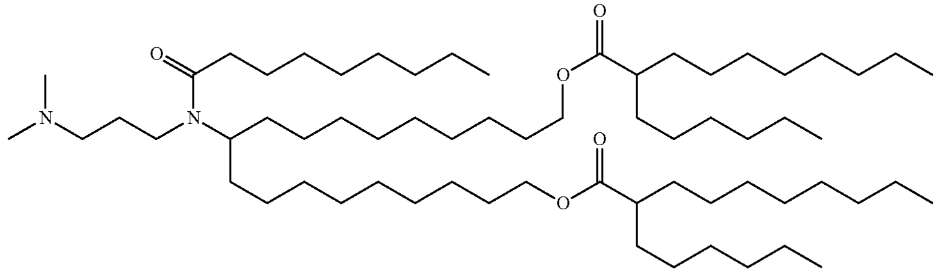 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

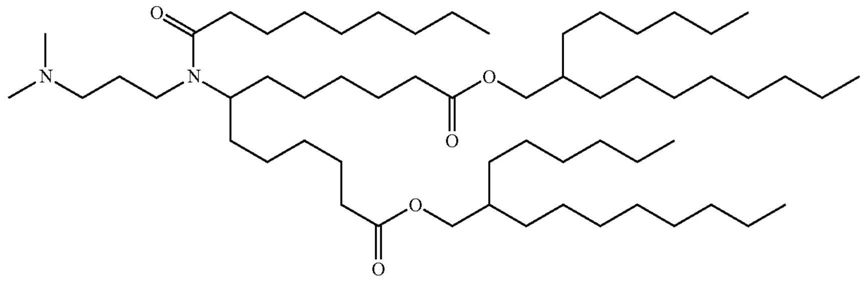 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

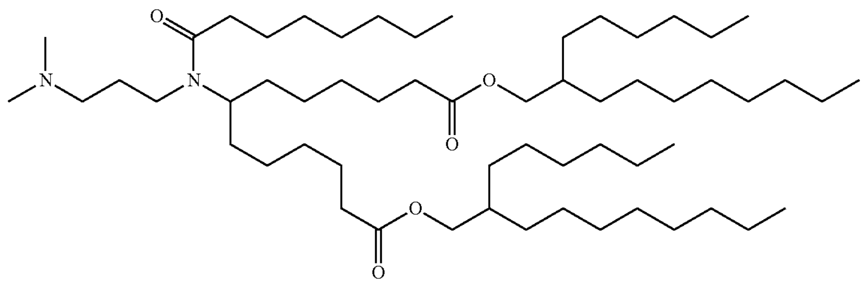 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

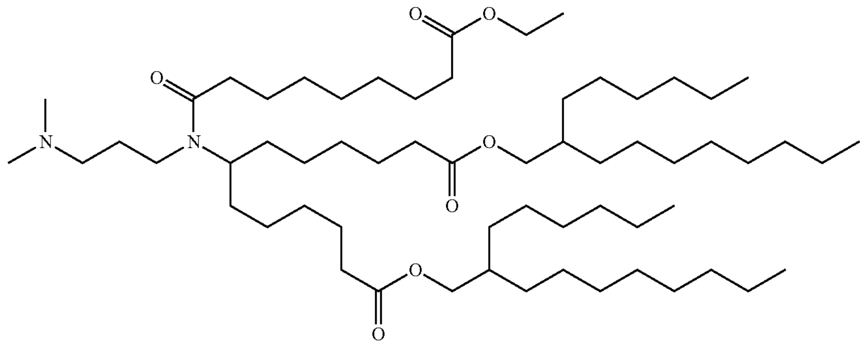 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

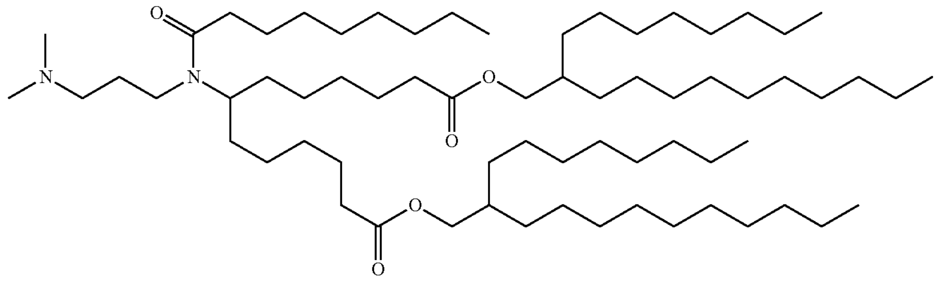 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

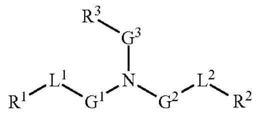

or a pharmaceutically acceptable salt thereof, wherein one of L' or $L^2$ is —O(C═O)—, —(C═O)O—, —C(═O)—, —O—, —S(O)$_x$, —S—S—, —C(═O)S—, —SC(═O)—, —NR$^a$C(═O)—, —C(═O)NR$^a$—, NR$^a$C(═O)NR$^a$—, —OC(═O)NR$^a$—, or —NR$^a$C(═O)O—; and the other of $L^1$ or $L^2$ is —O(C═O)—, —(C═O)O—, —C(═O)—, —O—, —S(O)$_x$, —S—S—, —C(═O)S—, SC(═O)—, —NR$^a$C(═O)—, —C(═O)NR$^a$—, —NR$^a$C(═O)NR$^a$—, —OC(═O)NR$^a$— or —NR$^a$C(═O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, $OR^5$, CN, —C(═O)OR$^4$, —OC(═O)R$^4$ or —NR$^5$C(═O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

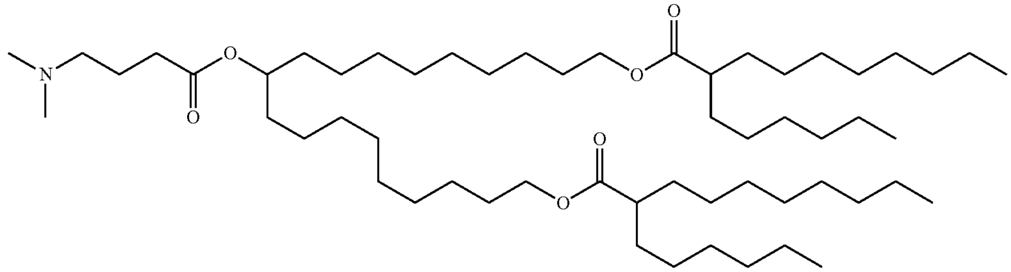 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

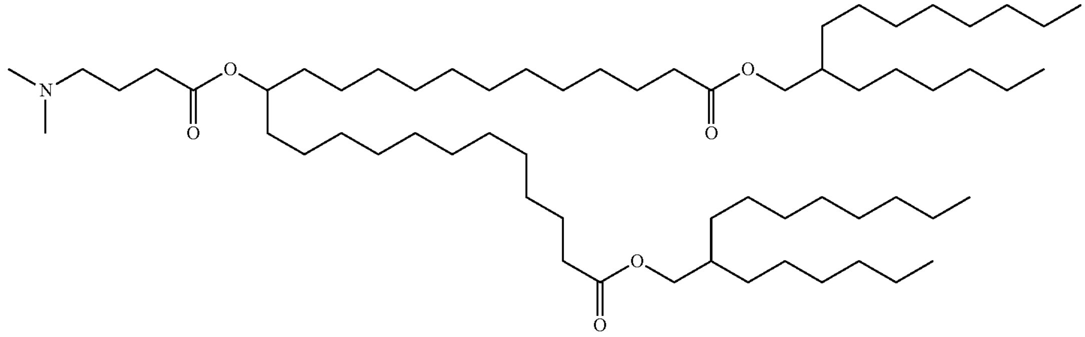 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

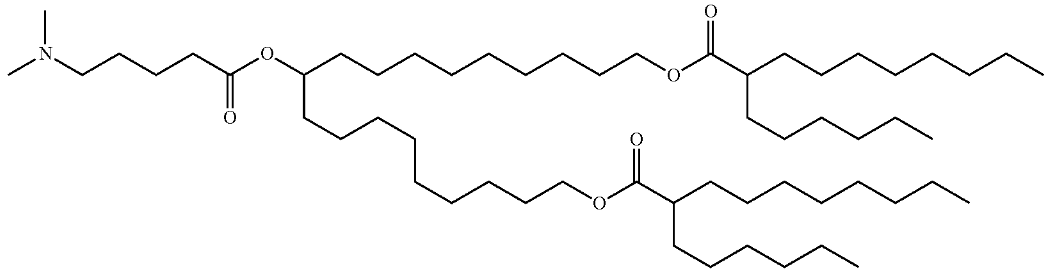 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

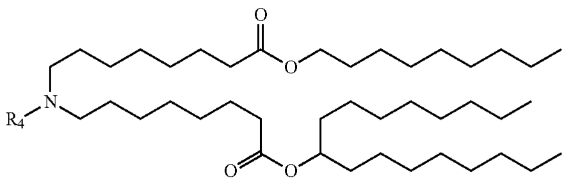

,

-continued

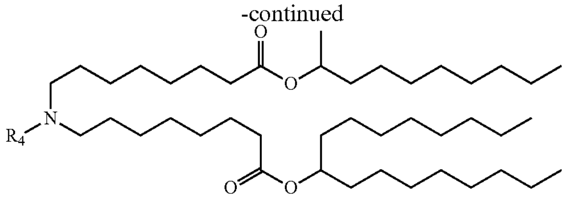

,

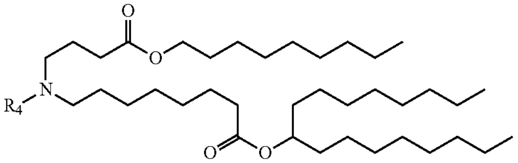

, and

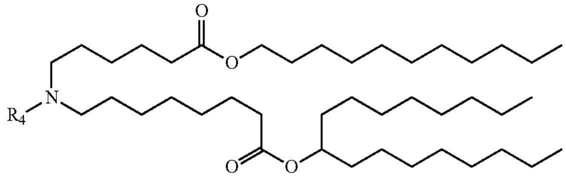

, and pharmaceutically acceptable salts thereof. For any one of these four formulas, $R_4$ is independently selected from $-(CH_2)_nQ$ and $-(CH_2)_nCHQR$; Q is selected from the group consisting of —OR, —OH, $-O(CH_2)_nN(R)_2$, —OC(O)R, $-CX_3$, —CN, —N(R)C(O)R, —N(H)C(O)R, $-N(R)S(O)_2R$, $-N(H)S(O)_2R$, $-N(R)C(O)N(R)_2$, $-N(H)C(O)N(R)_2$, —N(H)C(O)N(H)(R), $-N(R)C(S)N(R)_2$, $-N(H)C(S)N(R)_2$, —N(H)C(S)N(H)(R), and a heterocycle; and n is 1, 2, or 3. In certain embodiments, the compositions and methods of the present invention include a cationic lipid having a compound structure of:

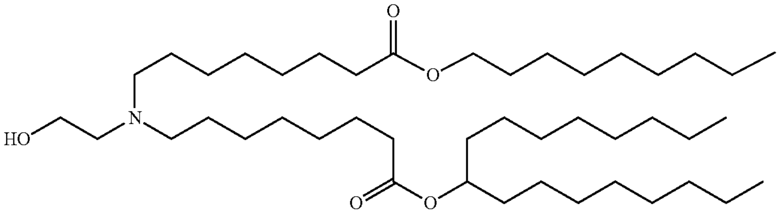 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

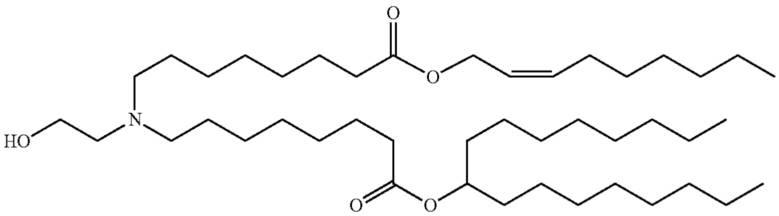 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

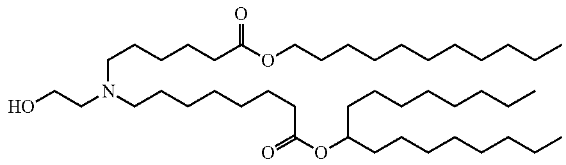 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

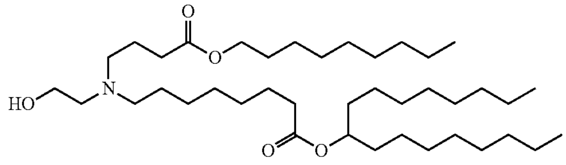 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

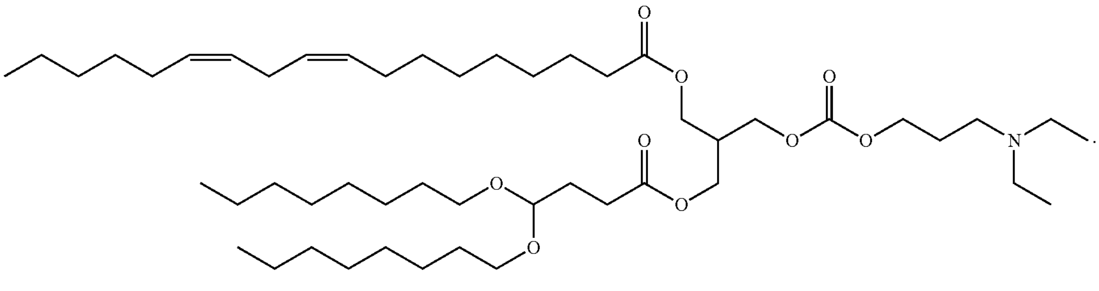 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

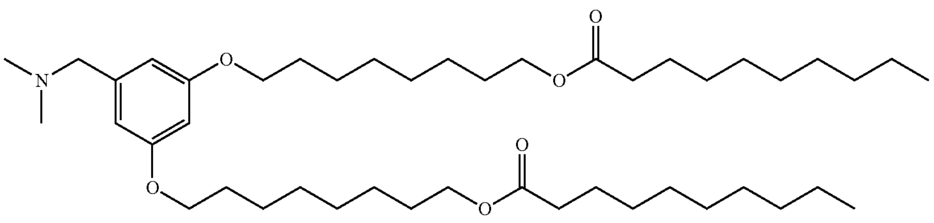 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

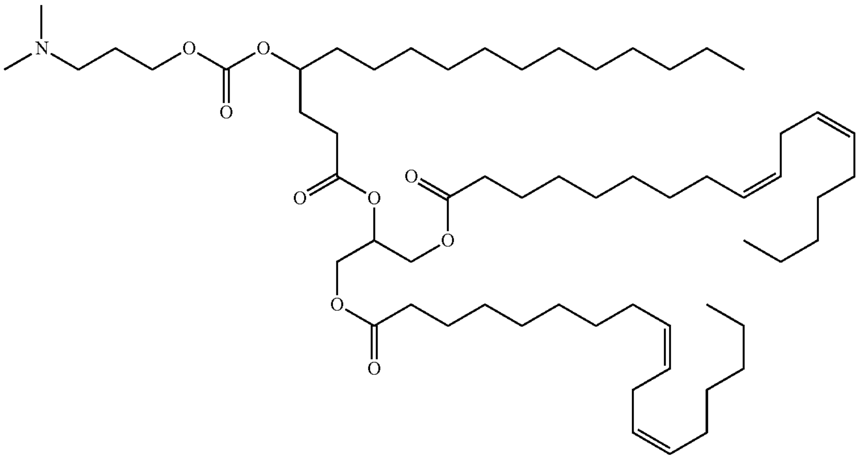 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

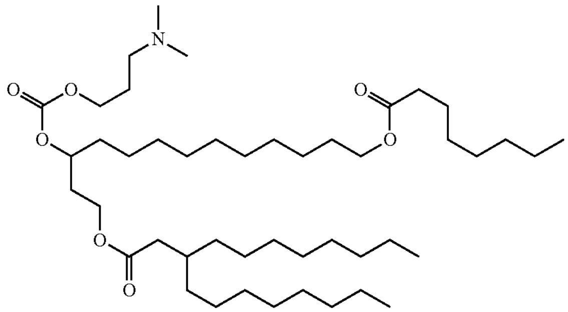 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

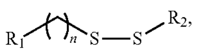

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

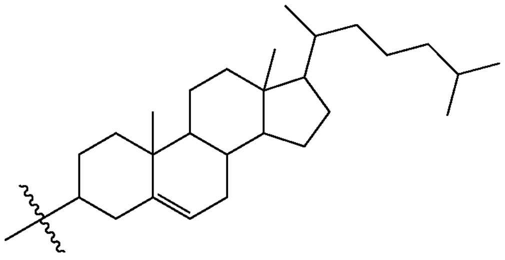

and

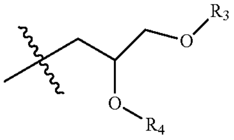

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

(HGT4001)

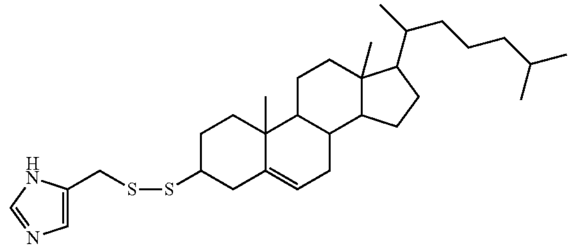

and pharmaceutically acceptable salts thereof. In certain embodiments, the compositions and methods of the present invention include a cationic lipid, "HGT4002", having a compound structure of:

(HGT4002)

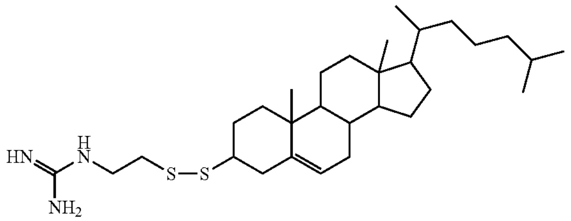

and pharmaceutically acceptable salts thereof. In certain embodiments, the compositions and methods of the present invention include a cationic lipid, "HGT4003", having a compound structure of:

(HGT4003)

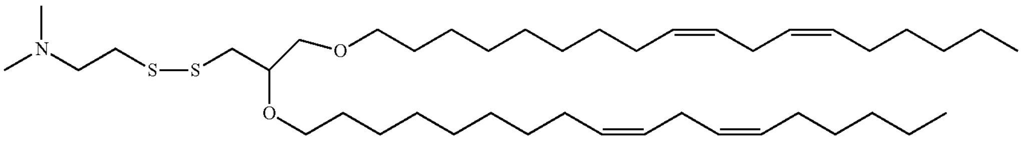

and pharmaceutically acceptable salts thereof. In certain embodiments, the compositions and methods of the present invention include a cationic lipid, "HGT4004", having a compound structure of:

(HGT4004)

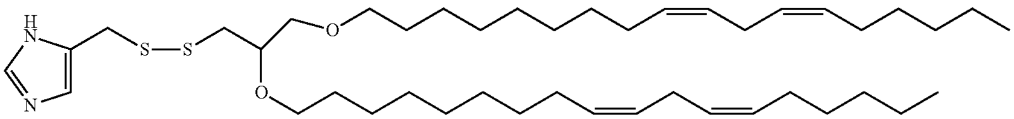

and pharmaceutically acceptable salts thereof. In certain embodiments, the compositions and methods of the present invention include a cationic lipid "HGT4005", having a compound structure of:

(HGT4005)

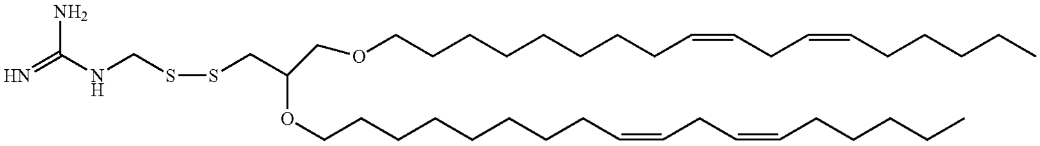

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional Application No. 62/672,194. In certain embodiments, the compositions and methods of the present invention include a cationic lipid that has a structure according to Formula (I'),

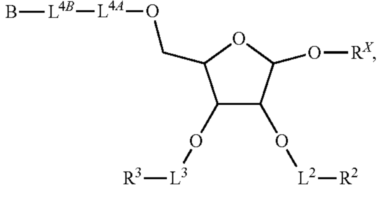

(I')

wherein:

$R^X$ is independently —H, or $-L^{5A}-L^{5B}-B'$;

each of $L^1$, $L^2$, and $L^3$ is independently a covalent bond, —C(O)—, —C(O)O—, —C(O)S—, or —C(O)$NR^L$—;

each $L^{4A}$ and $L^{5A}$ is independently —C(O)—, —C(O)O—, or —C(O)$NR^L$—;

each $L^{4B}$ and $L^{5B}$ is independently $C_1$-$C_{20}$ alkylene; $C_2$-$C_{20}$ alkenylene; or $C_2$-$C_{20}$ alkynylene;

each B and B' is $NR^4R^5$ or a 5- to 10-membered nitrogen-containing heteroaryl;

each $R^1$, $R^2$, and $R^3$ is independently $C_6$-$C_{30}$ alkyl, $C_6$-$C_{30}$ alkenyl, or $C_6$-$C_{30}$ alkynyl;

each $R^4$ and $R^5$ is independently hydrogen, $C_1$-$C_{10}$ alkyl; $C_2$-$C_{10}$ alkenyl; or $C_2$-$C_{10}$ alkynyl; and each $R^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of 62/672,194, having a compound structure of:

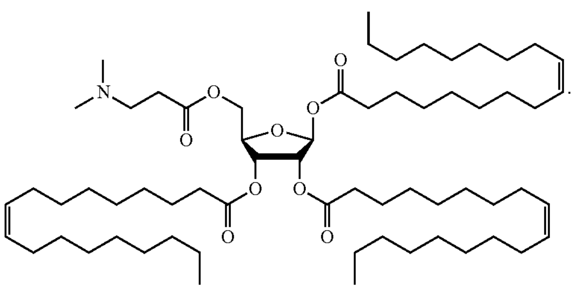

("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido)ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethyl-1-(cis,cis-9',1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoylcarbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N,N-dimethyl-3-[(9Z,12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z,12Z)-octadeca-9,12-dien-1-yloxy]propan-1-amine ("Octyl-CLinDMA (2R)"); (2S)-2-((8-[(3P)-cholest-5-en-3-yloxy]octyl)oxy)-N, fsl-dimethyh3-[(9Z,12Z)-octadeca-9,12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,12-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)—N,N-dimethyl-2,2-di((9Z,12Z)-octadeca-9,12-dienyl)tetrahydro-3aH-cyclopenta[d][1,3]dioxol-5-amine ("ALNY-100") and/or 4,7,13-tris(3-oxo-3-(undecylamino)propyl)-N1,N16-diundecyl-4,7,10,13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle.

Non-Cationic/Helper Lipids

In some embodiments, a suitable lipid solution includes one or more non-cation/helper lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), di stearoyl-phosphatidylethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other lipids, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

In some embodiments, non-cationic lipids may constitute at least about 5%, 10%, 15%, 20%, 25%, 30%, 35%, 40%, 45%, 50%, 55%, 60%, 65% or 70% of the total lipids in a suitable lipid solution by weight or by molar. In some embodiments, non-cationic lipid(s) constitute(s) about 30-50% (e.g., about 30-45%, about 30-40%, about 35-50%, about 35-45%, or about 35-40%) of the total lipids in a suitable lipid solution by weight or by molar.

In some embodiments, one or more non-cationic lipids are used in the process described herein. In some embodiments, the one or more non-cationic lipids comprise a non-cationic lipid selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)), and combinations thereof Cholesterol-Based Lipids In some embodiments, a suitable lipid solution includes one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the lipid nanoparticle may be greater than 5%, greater than 10%, greater than 20%, greater than 30%, or greater than 40%.

In some embodiments, cholesterol-based lipid(s) constitute(s) at least about 5%, 10%, 20%, 30%, 40%, 50%, 60%, or 70% of the total lipids in a suitable lipid solution by weight or by molar. In some embodiments, cholesterol-based lipid(s) constitute(s) about 30-50% (e.g., about 30-45%, about 30-40%, about 35-50%, about 35-45%, or about 35-40%) of the total lipids in a suitable lipid solution by weight or by molar.

PEGylated Lipids

In some embodiments, a suitable lipid solution includes one or more PEGylated lipids. The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000](C8 PEG-2000 ceramide) is also contemplated by the present invention, either alone or preferably in combination with other lipid formulations together which comprise the transfer vehicle (e.g., a lipid nanoparticle). Contemplated PEG-modified lipids include, but are not limited to, a polyethylene glycol chain of up to 5 kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEG-modified lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; ICE, DOPE, cholesterol and DMG-PEG2K; or ICE, DOPE, and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5. In some embodiments, the ratio of sterol lipid(s) to non-cationic lipid(s) to PEG-modified lipid(s) is 50:45:5. In some embodiments, the ratio of sterol lipid(s) to non-cationic lipid(s) to PEG-modified lipid(s) is 50:40:10. In some embodiments, the ratio of sterol lipid(s) to non-cationic lipid(s) to PEG-modified lipid(s) is 55:40:5. In some embodiments, the ratio of sterol lipid(s) to non-cationic lipid(s) to PEG-modified lipid(s) is 55:35:10. In some embodiments, the ratio of sterol lipid(s) to non-cationic lipid(s) to PEG-modified lipid(s) is 60:35:5. In some embodiments, the ratio of sterol lipid(s) to non-cationic lipid(s) to PEG-modified lipid(s) is 60:30:10.

In some embodiments, a suitable liposome for the present invention comprises ICE and DOPE at an ICE:DOPE molar ratio of >1:1. In some embodiments, the ICE:DOPE molar ratio is <2.5:1. In some embodiments, the ICE:DOPE molar ratio is between 1:1 and 2.5:1. In some embodiments, the ICE:DOPE molar ratio is approximately 1.5:1. In some embodiments, the ICE:DOPE molar ratio is approximately 1.7:1. In some embodiments, the ICE:DOPE molar ratio is approximately 2:1. In some embodiments, a suitable liposome for the present invention comprises ICE and DMG-PEG-2K at an ICE:DMG-PEG-2K molar ratio of >10:1. In some embodiments, the ICE:DMG-PEG-2K molar ratio is <16:1. In some embodiments, the ICE:DMG-PEG-2K molar ratio is approximately 12:1. In some embodiments, the ICE:DMG-PEG-2K molar ratio is approximately 14:1. In some embodiments, a suitable liposome for the present invention comprises DOPE and DMG-PEG-2K at a DOPE:DMG-PEG-2K molar ratio of >5:1. In some embodiments, the DOPE:DMG-PEG-2K molar ratio is <11:1. In some embodiments, the DOPE:DMG-PEG-2K molar ratio is approximately 7:1. In some embodiments, the DOPE:DMG-PEG-2K molar ratio is approximately 10:1. In some embodiments, a suitable liposome for the present invention comprises ICE, DOPE and DMG-PEG-2K at an ICE:DOPE:DMG-PEG-2K molar ratio of 50:45:5. In some embodiments, a suitable liposome for the present invention comprises ICE, DOPE and DMG-PEG-2K at an ICE:DOPE:DMG-PEG-2K molar ratio of 50:40:10. In some embodiments, a suitable liposome for the present invention comprises ICE, DOPE and DMG-PEG-2K at an ICE:DOPE:DMG-PEG-2K molar ratio of 55:40:5. In some embodiments, a suitable liposome for the present invention comprises ICE, DOPE and DMG-PEG-2K at an ICE:DOPE:DMG-PEG-2K molar ratio of 55:35:10. In some embodiments, a suitable liposome for the present invention comprises ICE, DOPE and DMG-PEG-2K at an ICE:DOPE:DMG-PEG-2K molar ratio of 60:35:5. In some embodiments, a suitable liposome for the present invention comprises ICE, DOPE and DMG-PEG-2K at an ICE:DOPE:DMG-PEG-2K molar ratio of 60:30:10.

In some embodiments, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention. Contemplated PEG-modified lipids include, but are not limited to, a polyethylene glycol chain of up to 2 kDa, up to 3 kDa, up to 4 kDa or up to 5 kDa in length covalently attached to a lipid with alkyl chain(s) of $C_6$-$C_{20}$ length. In some embodiments, a PEG-modified or PEGylated lipid is PEGylated cholesterol or PEG-2K. In some embodiments, particularly useful exchangeable lipids are PEG-ceramides having shorter acyl chains (e.g., $C_{14}$ or $C_{18}$).

PEG-modified phospholipid and derivatized lipids may constitute no greater than about 0.5%, 1%, 1.5%, 2%, 2.5%, 3%, 3.5%, 4%, 4.5% or 5% of the total lipids in a suitable lipid solution by weight or by molar. In some embodiments, PEG-modified lipids may constitute about 5% or less of the total lipids in a suitable lipid solution by weight or by molar concentration. In some embodiments, PEG-modified lipids may constitute about 4% or less of the total lipids in a suitable lipid solution by weight or by molar concentration. In some embodiments, PEG-modified lipids typically constitute 3% or less of total lipids in a suitable lipid solution by weight or by molar concentration. In some embodiments, PEG-modified lipids typically constitute 2% or less of total lipids in a suitable lipid solution by weight or by molar concentration. In some embodiments, PEG-modified lipids typically constitute 1% or less of total lipids in a suitable lipid solution by weight or by molar concentration. In some embodiments, PEG-modified lipids constitute about 1-5%, about 1-4%, about 1-3%, or about 1-2%) of the total lipids in a suitable lipid solution by weight or by molar concentration. In some embodiments, PEG modified lipids constitute about 0.01-3% (e.g., about 0.01-2.5%, 0.01-2%, 0.01-1.5%, 0.01-1%) of the total lipids in a suitable lipid solution by weight or by molar concentration.

Various combinations of lipids, i.e., cationic lipids, non-cationic lipids, PEG-modified lipids and optionally cholesterol, that can used to prepare, and that are comprised in, preformed lipid nanoparticles are described in the literature and herein. For example, a suitable lipid solution may contain cKK-E12, DOPE, cholesterol, and DMG-PEG2K; $C_{12}$-200, DOPE, cholesterol, and DMG-PEG2K; HGT5000, DOPE, cholesterol, and DMG-PEG2K; HGT5001, DOPE, cholesterol, and DMG-PEG2K; cKK-E12, DPPC, cholesterol, and DMG-PEG2K; $C_{12}$-200, DPPC, cholesterol, and DMG-PEG2K; HGT5000, DPPC, cholesterol, and DMG-PEG2K; HGT5001, DPPC, cholesterol, and DMG-PEG2K; or ICE, DOPE and DMG-PEG2K. Additional combinations of lipids are described in the art, e.g., PCT/US17/61100, filed on Nov. 10, 2017, published as WO 2018/089790; entitled "Novel ICE-based Lipid Nanoparticle Formulation for Delivery of mRNA,"; PCT/US18/21292, filed on Mar. 7, 2018, published as WO 2018/165257, entitled "PolyAnionic Delivery of Nucleic Acids"; PCT/US18/36920, filed on Jun. 11, 2018, entitled, "Poly (Phosphoesters) for Delivery of Nucleic Acids." The selection of cationic lipids, non-cationic lipids and/or PEG-modified lipids which comprise the lipid mixture as well as the relative molar ratio of such lipids to each other, is based upon the characteristics of the selected lipid(s) and the nature of the and the characteristics of the mRNA to be encapsulated. Additional considerations include, for example, the saturation of the alkyl chain, as well as the size, charge, pH, pKa, fusogenicity and toxicity of the selected lipid(s). Thus the molar ratios may be adjusted accordingly.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

Provided Nanoparticles Encapsulating mRNA

A process according to the present invention results in more homogeneous and smaller particle sizes (e.g., particle sizes of about 75-150 nm (e.g. 75, 80, 85, 90, 95, 100, 105, 110, 115, 120, 125, 130, 135, 140, 145, or 150 nm) as well as significantly improved encapsulation efficiency and/or mRNA recovery rate as compared to a prior art process.

Thus, the present invention provides a composition comprising purified nanoparticles described herein. In some embodiments, a majority of purified nanoparticles in a composition, i.e., greater than about 50%, 55%, 60%, 65%, 70%, 75%, 80%, 85%, 90%, 95%, 96%, 97%, 98%, or 99% of the purified nanoparticles, have a size less than about 100 nm (e.g., less than about 95 nm, about 90 nm, about 85 nm, about 80 nm, about 75 nm, about 70 nm, about 65 nm, about 60 nm, about 55 nm, or about 50 nm). In some embodiments, substantially all of the purified nanoparticles have a size less than 100 nm (e.g., less than about 95 nm, about 90 nm, about 85 nm, about 80 nm, about 75 nm, about 70 nm, about 65 nm, about 60 nm, about 55 nm, or about 50 nm).

In addition, more homogeneous nanoparticles with narrow particle size range are achieved by a process of the present invention. For example, greater than about 70%, 75%, 80%, 85%, 90%, 95%, 96%, 97%, 98%, 99% of the purified nanoparticles in a composition provided by the present invention have a size ranging from about 40-90 nm (e.g., about 40-85 nm, about 40-80 nm, about 40-75 nm, about 40-70 nm, about 40-65 nm, or about 40-60 nm). In some embodiments, substantially all of the purified nanoparticles have a size ranging from about 40-90 nm (e.g., about 40-85 nm, about 40-80 nm, about 40-75 nm, about 40-70 nm, about 40-65 nm, or about 40-60 nm).

In some embodiments, the dispersity, or measure of heterogeneity in size of molecules (PDI), of nanoparticles in a composition provided by the present invention is less than about 0.3 (e.g., less than about 0.3, 0.2, 0.15, 0.14, 0.13, 0.12, 0.11, 0.10, 0.09, or 0.08).

In some embodiments, greater than about 75%, 80%, 85%, 90%, 95%, 96%, 97%, 98%, or 99% of the purified lipid nanoparticles in a composition provided by the present invention encapsulate an mRNA within each individual particle. In some embodiments, substantially all of the purified lipid nanoparticles in a composition encapsulate an mRNA within each individual particle.

In some embodiments, a composition according to the present invention contains at least about 1 mg, 5 mg, 10 mg, 100 mg, 500 mg, or 1000 mg of encapsulated mRNA. In some embodiments, a process according to the present invention results in greater than about 60%, 65%, 70%, 75%, 80%, 85%, 90%, 95%, 96%, 97%, 98%, or 99% recovery of mRNA.

This invention is further illustrated by the following examples that should not be construed as limiting. The contents of all references, patents, and published patent applications cited throughout this application are herein incorporated by reference in their entirety for all purposes.

Purification

In some embodiments, the encapsulated nucleic acids (e.g. encapsulated mRNA) in lipid nanoparticles are further purified and/or concentrated. Various purification methods may be used. In some embodiments, lipid nanoparticles are purified using Tangential Flow Filtration. Tangential flow filtration (TFF), also referred to as cross-flow filtration, is a type of filtration wherein the material to be filtered is passed tangentially across a filter rather than through it. In TFF, undesired permeate passes through the filter, while the desired retentate passes along the filter and is collected downstream. It is important to note that the desired material is typically contained in the retentate in TFF, which is the opposite of what one normally encounters in traditional-dead end filtration.

Depending upon the material to be filtered, TFF is usually used for either microfiltration or ultrafiltration. Microfiltration is typically defined as instances where the filter has a pore size of between 0.05 μm and 1.0 μm, inclusive, while ultrafiltration typically involves filters with a pore size of less than 0.05 μm. Pore size also determines the nominal molecular weight limits (NMWL), also referred to as the molecular weight cut off (MWCO) for a particular filter, with microfiltration membranes typically having NMWLs of greater than 1,000 kilodaltons (kDa) and ultrafiltration filters having NMWLs of between 1 kDa and 1,000 kDa.

A principal advantage of tangential flow filtration is that non-permeable particles that may aggregate in and block the filter (sometimes referred to as "filter cake") during traditional "dead-end" filtration, are instead carried along the surface of the filter. This advantage allows tangential flow filtration to be widely used in industrial processes requiring continuous operation since down time is significantly reduced because filters do not generally need to be removed and cleaned.

Tangential flow filtration can be used for several purposes including concentration and diafiltration, among others. Concentration is a process whereby solvent is removed from a solution while solute molecules are retained. In order to effectively concentrate a sample, a membrane having a NMWL or MWCO that is substantially lower than the molecular weight of the solute molecules to be retained is used. Generally, one of skill may select a filter having a NMWL or MWCO of three to six times below the molecular weight of the target molecule(s).

Diafiltration is a fractionation process whereby small undesired particles are passed through a filter while larger desired nanoparticles are maintained in the retentate without changing the concentration of those nanoparticles in solution. Diafiltration is often used to remove salts or reaction buffers from a solution. Diafiltration may be either continuous or discontinuous. In continuous diafiltration, a diafiltration solution is added to the sample feed at the same rate that filtrate is generated. In discontinuous diafiltration, the solution is first diluted and then concentrated back to the starting concentration. Discontinuous diafiltration may be repeated until a desired concentration of nanoparticles is reached.

In some embodiments, purification and/or concentration steps include dialysis, gel filtration, centrifugation (e.g. use of Amicon centrifugal filters), vacuum, and pressure-press (e.g. French press).

Purified and/or concentrated lipid nanoparticles may be formulated in a desired buffer such as, for example, PBS.

Therapeutic Indications

In some embodiments, the present invention can be used to encapsulate mRNA in lipids, thus producing lipid encapsulated mRNA for use in the treatment of various disorders, diseases, conditions and/or syndromes. Non-limiting examples of select uses of the invention as described herein are described in the paragraphs that follow.

In some embodiments, the present invention provides a method for producing a therapeutic composition comprising lipid encapsulated mRNA that encodes a peptide or polypeptide for use in the delivery to or treatment of a human subject. In some embodiments, therapeutic composition comprising lipid encapsulated mRNA is used for delivery in the lung of a subject or a lung cell. In certain embodiments, the present invention provides a method for producing a therapeutic composition comprising lipid encapsulated mRNA that encodes an endogenous protein which may be deficient or non-functional in a subject. In certain embodiments, the present invention provides a method for producing a therapeutic composition comprising lipid encapsulated mRNA that encodes an endogenous protein which may be deficient or non-functional in a subject.

In certain embodiments, the present invention provides a method for producing a therapeutic composition comprising lipid encapsulated mRNA that encodes a peptide or polypeptide for use in the delivery to or treatment of the lung of a subject or a lung cell. In certain embodiments, the present invention is useful in a method for manufacturing mRNA encoding cystic fibrosis transmembrane conductance regulator, CFTR. The CFTR mRNA is delivered to the lung of a subject in need in a therapeutic composition for treating cystic fibrosis. In certain embodiments, the present invention provides a method for producing a therapeutic composition comprising lipid encapsulated mRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methyl malonic acidemia, or associated with any other metabolic disorder for which delivery to or treatment of the liver or a liver cell with enriched full-length mRNA provides therapeutic benefit.

In certain embodiments, the present invention provides a method for producing a therapeutic composition comprising lipid encapsulated mRNA that encodes for a protein associated with a urea cycle disorder. In certain embodiments, the present invention provides a method for producing a therapeutic composition comprising lipid encapsulated mRNA that encodes for ornithine transcarbamylase (OTC) protein. In certain embodiments, the present invention provides a method for producing a therapeutic composition comprising lipid encapsulated mRNA that encodes for argininosuccinate synthetase 1 protein. In certain embodiments, the present invention provides a method for producing a therapeutic composition comprising lipid encapsulated mRNA that encodes for carbamoyl phosphate synthetase I protein. In certain embodiments, the present invention provides a method for producing a therapeutic composition comprising lipid encapsulated mRNA that encodes for argininosuccinate lyase protein. In certain embodiments, the present invention provides a method for producing a therapeutic composition comprising lipid encapsulated mRNA that encodes for arginase protein.

In certain embodiments, the present invention provides a method for producing a therapeutic composition comprising lipid encapsulated mRNA that encodes for a protein associated with a lysosomal storage disorder. In certain embodiments, the present invention provides a method for producing a therapeutic composition comprising lipid encapsulated mRNA that encodes for alpha galactosidase protein. In certain embodiments, the present invention provides a method for producing a therapeutic composition comprising lipid encapsulated mRNA that encodes for glucocerebrosidase protein. In certain embodiments, the present invention provides a method for producing a therapeutic composition comprising lipid encapsulated mRNA that encodes for iduronate-2-sulfatase protein. In certain embodiments, the present invention provides a method for producing a therapeutic composition comprising lipid encapsulated mRNA that encodes for iduronidase protein. In certain embodiments, the present invention provides a method for producing a therapeutic composition comprising lipid encapsulated mRNA that encodes for N-acetyl-alpha-D-glucosaminidase protein. In certain embodiments, the present invention provides a method for producing a therapeutic composition comprising lipid encapsulated mRNA that encodes for heparan N-sulfatase protein. In certain embodiments, the present invention provides a method for producing a therapeutic composition comprising lipid encapsulated mRNA that encodes for galactosamine-6 sulfatase protein. In certain embodiments, the present invention provides a method for producing a therapeutic composition comprising lipid encapsulated mRNA that encodes for beta-galactosidase protein. In certain embodiments, the present invention provides a method for producing a therapeutic composition comprising lipid encapsulated mRNA that encodes for lysosomal lipase protein. In certain embodiments, the present invention provides a method for producing a therapeutic composition comprising lipid encapsulated mRNA that encodes for arylsulfatase B (N-acetylgalactosamine-4-sulfatase) protein. In certain embodiments, the present invention provides a method for producing a therapeutic composition comprising lipid encapsulated mRNA that encodes for transcription factor EB (TFEB).

In certain embodiments, the present invention provides a method for producing a therapeutic composition comprising lipid encapsulated mRNA that encodes for a protein associated with a glycogen storage disorder. In certain embodiments, the present invention provides a method for producing a therapeutic composition comprising lipid encapsulated mRNA that encodes for acid alpha-glucosidase protein. In certain embodiments, the present invention provides a method for producing a therapeutic composition comprising lipid encapsulated mRNA that encodes for glucose-6-phosphatase (G6PC) protein. In certain embodiments, the present invention provides a method for producing a therapeutic composition comprising lipid encapsulated mRNA that encodes for liver glycogen phosphorylase protein. In certain embodiments, the present invention provides a method for producing a therapeutic composition comprising lipid encapsulated mRNA that encodes for muscle phosphoglycerate mutase protein. In certain embodiments, the present invention provides a method for producing a therapeutic composition comprising lipid encapsulated mRNA that encodes for glycogen debranching enzyme.

In certain embodiments, the present invention provides a method for producing a therapeutic composition comprising lipid encapsulated mRNA that encodes for a protein associated with amino acid metabolism. In certain embodiments, the present invention provides a method for producing a therapeutic composition comprising lipid encapsulated mRNA that encodes for phenylalanine hydroxylase enzyme. In certain embodiments, the present invention provides a method for producing a therapeutic composition comprising lipid encapsulated mRNA that encodes for glutaryl-CoA dehydrogenase enzyme. In certain embodiments, the present invention provides a method for producing a therapeutic composition comprising lipid encapsulated mRNA that encodes for propionyl-CoA caboxylase enzyme. In certain embodiments, the present invention provides a method for producing a therapeutic composition comprising lipid encapsulated mRNA that encodes for oxalase alanine-glyoxylate aminotransferase enzyme.

In certain embodiments, the present invention provides a method for producing a therapeutic composition comprising lipid encapsulated mRNA that encodes for a protein associated with a lipid metabolism or fibrotic disorder. In certain embodiments, the present invention provides a method for producing a therapeutic composition comprising lipid encapsulated mRNA that encodes for an mTOR inhibitor. In certain embodiments, the present invention provides a method for producing a therapeutic composition comprising lipid encapsulated mRNA that encodes for ATPase phospholipid transporting 8B1 (ATP8B1) protein. In certain embodiments, the present invention provides a method for producing a therapeutic composition comprising lipid encapsulated mRNA that encodes for one or more NF-kappa B inhibitors, such as one or more of I-kappa B alpha, interferon-related development regulator 1 (IFRD1), and Sirtuin 1 (SIRT1). In certain embodiments, the present invention provides a method for producing a therapeutic composition comprising lipid encapsulated mRNA that encodes for PPAR-gamma protein or an active variant.

In certain embodiments, the present invention provides a method for producing a therapeutic composition comprising lipid encapsulated mRNA that encodes for a protein associated with methyl malonic acidemia. For example, in certain embodiments, the present invention provides a method for producing a therapeutic composition comprising lipid encapsulated mRNA that encodes for methyl malonyl CoA mutase protein. In certain embodiments, the present invention provides a method for producing a therapeutic composition comprising lipid encapsulated mRNA that encodes for methylmalonyl CoA epimerase protein.

In certain embodiments, the present invention provides a method for producing a therapeutic composition comprising lipid encapsulated mRNA for which delivery to or treatment of the liver can provide therapeutic benefit. In certain embodiments, the present invention provides a method for producing a therapeutic composition comprising lipid encapsulated mRNA that encodes for ATP7B protein, also known as Wilson disease protein. In certain embodiments, the present invention provides a method for producing a therapeutic composition comprising lipid encapsulated mRNA that encodes for porphobilinogen deaminase enzyme. In certain embodiments, the present invention provides a method for producing a therapeutic composition comprising lipid encapsulated mRNA that encodes for one or clotting enzymes, such as Factor VIII, Factor IX, Factor VII, and Factor X. In certain embodiments, the present invention provides a method for producing a therapeutic composition comprising lipid encapsulated mRNA that encodes for human hemochromatosis (HFE) protein.

In certain embodiments, the present invention provides a method for producing a therapeutic composition comprising lipid encapsulated mRNA that encodes a peptide or polypeptide for use in the delivery to or treatment of the cardiovascular conditions of a subject or a cardiovascular cell. In certain embodiments, the present invention provides a method for producing a therapeutic composition comprising lipid encapsulated mRNA that encodes for vascular endothelial growth factor A protein. In certain embodiments, the present invention provides a method for producing a therapeutic composition comprising lipid encapsulated mRNA that encodes for relaxin protein. In certain embodiments, the present invention provides a method for producing a therapeutic composition comprising lipid encapsulated mRNA that encodes for bone morphogenetic protein-9 protein. In certain embodiments, the present invention provides a method for producing a therapeutic composition comprising lipid encapsulated mRNA that encodes for bone morphogenetic protein-2 receptor protein.

In certain embodiments, the present invention provides a method for producing a therapeutic composition comprising lipid encapsulated mRNA that encodes a peptide or polypeptide for use in the delivery to or treatment of the muscle of a subject or a muscle cell. In certain embodiments, the present invention provides a method for producing a therapeutic composition comprising lipid encapsulated mRNA that encodes for dystrophin protein. In certain embodiments, the present invention provides a method for producing a therapeutic composition comprising lipid encapsulated mRNA that encodes for frataxin protein. In certain embodiments, the present invention provides a method for producing a therapeutic composition comprising lipid encapsulated mRNA that encodes a peptide or polypeptide for use in the delivery to or treatment of the cardiac muscle of a subject or a cardiac muscle cell. In certain embodiments, the present invention provides a method for producing a therapeutic composition comprising lipid encapsulated mRNA that encodes for a protein that modulates one or both of a potassium channel and a sodium channel in muscle tissue or in a muscle cell. In certain embodiments, the present invention provides a method for producing a therapeutic composition comprising lipid encapsulated mRNA that encodes for a protein that modulates a Kv7.1 channel in muscle tissue or in a muscle cell. In certain embodiments, the present invention provides a method for producing a therapeutic composition comprising lipid encapsulated mRNA that encodes for a protein that modulates a Nav1.5 channel in muscle tissue or in a muscle cell.

In certain embodiments, the present invention provides a method for producing a therapeutic composition comprising lipid encapsulated mRNA that encodes a peptide or polypeptide for use in the delivery to or treatment of the nervous system of a subject or a nervous system cell. For example, in certain embodiments, the present invention provides a method for producing a therapeutic composition comprising lipid encapsulated mRNA that encodes for survival motor neuron 1 protein. For example, in certain embodiments, the present invention provides a method for producing a therapeutic composition comprising lipid encapsulated mRNA that encodes for survival motor neuron 2 protein. In certain embodiments, the present invention provides a method for producing a therapeutic composition comprising lipid encapsulated mRNA that encodes for frataxin protein. In certain embodiments, the present invention provides a method for producing a therapeutic composition comprising lipid encapsulated mRNA that encodes for ATP binding cassette subfamily D member 1 (ABCD1) protein. In certain embodiments, the present invention provides a method for producing a therapeutic composition comprising lipid encapsulated mRNA that encodes for CLN3 protein.

In certain embodiments, the present invention provides a method for producing a therapeutic composition comprising lipid encapsulated mRNA that encodes a peptide or polypeptide for use in the delivery to or treatment of the blood or bone marrow of a subject or a blood or bone marrow cell. In certain embodiments, the present invention provides a method for producing a therapeutic composition comprising lipid encapsulated mRNA that encodes for beta globin protein. In certain embodiments, the present invention provides a method for producing a therapeutic composition comprising lipid encapsulated mRNA that encodes for Bruton's tyrosine kinase protein. In certain embodiments, the present invention provides a method for producing a therapeutic composition comprising lipid encapsulated mRNA that encodes for one or clotting enzymes, such as Factor VIII, Factor IX, Factor VII, and Factor X.

In certain embodiments, the present invention provides a method for producing a therapeutic composition comprising lipid encapsulated mRNA that encodes a peptide or polypeptide for use in the delivery to or treatment of the kidney of a subject or a kidney cell. In certain embodiments, the present invention provides a method for producing a therapeutic composition comprising lipid encapsulated mRNA that encodes for collagen type IV alpha 5 chain (COL4A5) protein.

In certain embodiments, the present invention provides a method for producing a therapeutic composition comprising lipid encapsulated mRNA that encodes a peptide or polypeptide for use in the delivery to or treatment of the eye of a subject or an eye cell. In certain embodiments, the present invention provides a method for producing a therapeutic composition comprising lipid encapsulated mRNA that encodes for ATP-binding cassette subfamily A member 4 (ABCA4) protein. In certain embodiments, the present invention provides a method for producing a therapeutic composition comprising lipid encapsulated mRNA that encodes for retinoschisin protein. In certain embodiments, the present invention provides a method for producing a therapeutic composition comprising lipid encapsulated mRNA that encodes for retinal pigment epithelium-specific 65 kDa (RPE65) protein. In certain embodiments, the present invention provides a method for producing a therapeutic composition comprising lipid encapsulated mRNA that encodes for centrosomal protein of 290 kDa (CEP290).

In certain embodiments, the present invention provides a method for producing a therapeutic composition comprising lipid encapsulated mRNA that encodes a peptide or polypeptide for use in the delivery of or treatment with a vaccine for a subject or a cell of a subject. For example, in certain embodiments, the present invention provides a method for producing a therapeutic composition comprising lipid encapsulated mRNA that encodes for an antigen from an infectious agent, such as a virus. In certain embodiments, the present invention provides a method for producing a therapeutic composition comprising lipid encapsulated mRNA that encodes for an antigen from influenza virus. In certain embodiments, the present invention provides a method for producing a therapeutic composition comprising lipid encapsulated mRNA that encodes for an antigen from respiratory syncytial virus. In certain embodiments, the present invention provides a method for producing a therapeutic composition comprising lipid encapsulated mRNA that encodes for an antigen from rabies virus. In certain embodiments, the present invention provides a method for producing a therapeutic composition comprising lipid encapsulated mRNA that encodes for an antigen from cytomegalovirus. In certain embodiments, the present invention provides a method for producing a therapeutic composition comprising lipid encapsulated mRNA that encodes for an antigen from rotavirus. In certain embodiments, the present invention provides a method for producing a therapeutic composition comprising lipid encapsulated mRNA that encodes for an antigen from a hepatitis virus, such as hepatitis A virus, hepatitis B virus, or hepatis C virus. In certain embodiments, the present invention provides a method for producing a therapeutic composition comprising lipid encapsulated mRNA that encodes for an antigen from human papillomavirus. In certain embodiments, the present invention provides a method for producing a therapeutic composition comprising lipid encapsulated mRNA that encodes for an antigen from a herpes simplex virus, such as herpes simplex virus 1 or herpes simplex virus 2. In certain embodiments, the present invention provides a method for producing a therapeutic composition comprising lipid encapsulated mRNA that encodes for an antigen from a human immunodeficiency virus, such as human immunodeficiency virus type 1 or human immunodeficiency virus type 2. In certain embodiments, the present invention provides a method for producing a therapeutic composition comprising lipid encapsulated mRNA that encodes for an antigen from a human metapneumovirus. In certain embodiments, the present invention provides a method for producing a therapeutic composition comprising lipid encapsulated mRNA that encodes for an antigen from a human parainfluenza virus, such as human parainfluenza virus type 1, human parainfluenza virus type 2, or human parainfluenza virus type 3. In certain embodiments, the present invention provides a method for producing a therapeutic composition comprising lipid encapsulated mRNA that encodes for an antigen from malaria virus. In certain embodiments, the present invention provides a method for producing a therapeutic composition comprising lipid encapsulated mRNA that encodes for an antigen from zika virus. In certain embodiments, the present invention provides a method for producing a therapeutic composition comprising lipid encapsulated mRNA that encodes for an antigen from chikungunya virus.

In certain embodiments, the present invention provides a method for producing a therapeutic composition comprising lipid encapsulated mRNA that encodes for an antigen associated with a cancer of a subject or identified from a cancer cell of a subject. In certain embodiments, the present invention provides a method for producing a therapeutic composition comprising lipid encapsulated mRNA that encodes for an antigen determined from a subject's own cancer cell, i.e., to provide a personalized cancer vaccine. In certain embodiments, the present invention provides a method for producing a therapeutic composition comprising lipid encapsulated mRNA that encodes for an antigen expressed from a mutant KRAS gene.

In certain embodiments, the present invention provides a method for producing a therapeutic composition comprising lipid encapsulated mRNA that encodes for an antibody. In certain embodiments, the antibody can be a bi-specific antibody. In certain embodiments, the antibody can be part of a fusion protein. In certain embodiments, the present invention provides a method for producing a therapeutic composition comprising lipid encapsulated mRNA that encodes for an antibody to OX40. In certain embodiments, the present invention provides a method for producing a therapeutic composition comprising lipid encapsulated mRNA that encodes for an antibody to VEGF. In certain embodiments, the present invention provides a method for producing a therapeutic composition comprising lipid encapsulated mRNA that encodes for an antibody to tissue necrosis factor alpha. In certain embodiments, the present invention provides a method for producing a therapeutic composition comprising lipid encapsulated mRNA that encodes for an antibody to CD3. In certain embodiments, the present invention provides a method for producing a therapeutic composition comprising lipid encapsulated mRNA that encodes for an antibody to CD19.

In certain embodiments, the present invention provides a method for producing a therapeutic composition comprising lipid encapsulated mRNA that encodes for an immunomodulator. In certain embodiments, the present invention provides a method for producing a therapeutic composition comprising lipid encapsulated mRNA that encodes for Interleukin 12. In certain embodiments, the present invention provides a method for producing a therapeutic composition comprising lipid encapsulated mRNA that encodes for Interleukin 23. In certain embodiments, the present invention provides a method for producing a therapeutic composition comprising lipid encapsulated mRNA that encodes for Interleukin 36 gamma. In certain embodiments, the present invention provides a method for producing a therapeutic composition comprising lipid encapsulated mRNA that encodes for a constitutively active variant of one or more stimulator of interferon genes (STING) proteins.

In certain embodiments, the present invention provides a method for producing a therapeutic composition comprising lipid encapsulated mRNA that encodes for an endonuclease. In certain embodiments, the present invention provides a method for producing a therapeutic composition comprising lipid encapsulated mRNA that encodes for an RNA-guided DNA endonuclease protein, such as Cas 9 protein. In certain embodiments, the present invention provides a method for producing a therapeutic composition comprising lipid encapsulated mRNA that encodes for a meganuclease protein. In certain embodiments, the present invention provides a method for producing a therapeutic composition comprising lipid encapsulated mRNA that encodes for a transcription activator-like effector nuclease protein. In certain embodiments, the present invention provides a method for producing a therapeutic composition comprising lipid encapsulated mRNA that encodes for a zinc finger nuclease protein.

In certain embodiments, the present invention provides a method for producing a therapeutic composition comprising lipid encapsulated mRNA that encodes for treating an ocular disease. In some embodiments, the method is used for producing a therapeutic composition comprising lipid encapsulated mRNA encoding retinoschisin.

EXAMPLES

The following examples, including the experiments conducted and results achieved are provided for illustrative purposes only and are not to be construed as limiting upon the present disclosure.

Lipid Materials

The formulations described in the following Examples, unless otherwise specified, contain a multi-component lipid mixture of varying ratios employing one or more cationic lipids, helper lipids (e.g. non-cationic lipids and/or cholesterol lipids), and PEGylated lipids designed to encapsulate various nucleic acid materials.

Example 1: Gravity-Based Nucleic Acid Encapsulation

This example illustrates a gravity-based nucleic acid encapsulation process. As used herein, Process A refers to a conventional method of encapsulating mRNA by mixing mRNA with a mixture of lipids, without first pre-forming the lipids into lipid nanoparticles. As used herein, Process B refers to a process of encapsulating messenger RNA (mRNA) by mixing pre-formed lipid nanoparticles with mRNA. As compared to Process B, Process A does not involve pre-formation of lipid nanoparticles. Process A and Process B include those described in WO2016004318 and WO2018089801, respectively, which are hereby incorporated by reference.

FIG. 1 illustrates an exemplary encapsulation process using the methods described herein. The exemplary encapsulation process of the present invention can be applied to both Process A and Process B. The exemplary process shown in FIG. 1 includes 1) a first reservoir to provide a desired nucleic acid in aqueous solution; 2) a second reservoir to provide a solution of lipids and/or lipid nanoparticles (LNPs); 3) conduits for the first and second reservoirs to allow for flow of nucleic acids, and lipids and/or LNPs; 4) a junction for mixing the nucleic acids and lipids and/or LNPs; and 5) a receptacle or conduit for collecting the mixed/encapsulated nucleic acids in LNPs.

The process uses gravity and atmospheric pressure as forces to drive the flow of liquid from Reservoir 1 (mRNA solution containing reservoir), and Reservoir 2 (lipids or LNP solution containing reservoir) through Conduit 1 (mRNA solution flow) and through Conduit 2 (lipid or LNP solution flow), respectively. The solutions from Reservoir 1 and Reservoir 2 meet at the junction (i.e. a "Y" connector or a "T" connector) and are thus mixed together at a specific flow rate. The mixing of the mRNA solution and the lipid or LNP containing solution results in the encapsulation of the mRNA in a lipid nanoparticle. The encapsulated mRNA is subsequently collected in a receptacle.

Figure 2A:
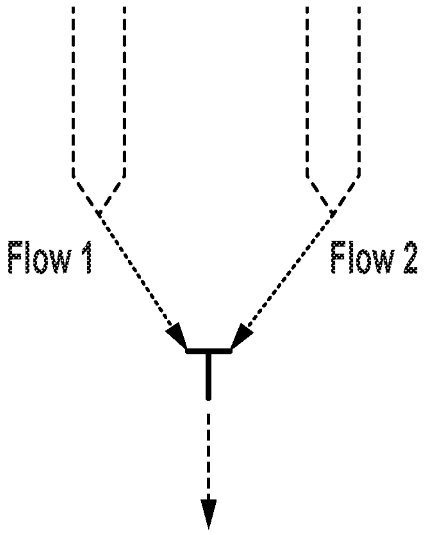
FIGS. 2A and 2B are schematics that depict an exemplary process comprising a "T" junction (FIG. 2A) or a "Y" junction (FIG. 2B) at the point of mixture.
Figure 2B:
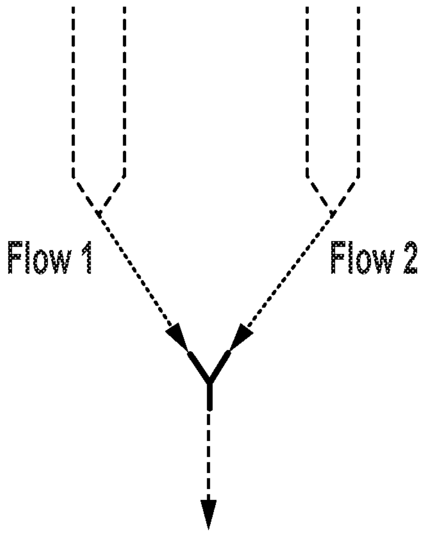

Various junctions can be used with the process disclosed herein. As illustrated in FIGS. 2A and 2B, respectively, options of junctions include, for example, use of a "T" connector or a "Y" connector.

This process was used to successfully encapsulate mRNA using various cationic lipids, including ones listed in Table 1, applying to both Process A and Process B. The measured atmospheric pressure and head pressure were essentially 0. The results of the encapsulation processes runs are shown in Table 1 below.

TABLE 1

Encapsulation of mRNA using a Gravity-Based Encapsulation Process

| Cationic lipid | Size (nm) | % mRNA encapsulation | PDI |
|---|---|---|---|
| cKK-E12 (1) | 99 | 79 | |
| MC3 (1) | 89 | 83 | |
| CCBene (1) | 102 | 87 | |
| cKK-E12 (2) | 72 | | 0.218 |
| OF-02/cKK-E18:2/ML7 | 82 | | 0.126 |
| cDD-TE-E12 | 93 | | 0.259 |
| MC3 (2) | 68 | | 0.156 |
| CCBene (2) | 69 | | 0.112 |
| RL2-DMP-07D | 84 | | 0.147 |
| ICE | 49 | | 0.283 |
| cKK-E12 (Process B) | 92 | | 0.133 |

* Process A was applied unless indicated otherwise.

As is shown in Table 1, the gravity encapsulation process resulted in encapsulation efficiencies of between about 79 and 87% for encapsulation with cKK-E12 and CCBene, respectively. Moreover, the sizes of the encapsulated mRNA ranged from about 49 nm to about 102 nm, with low PDI values, all below 0.3.

Example 2: Control of Liquid Flow Rate in the Process

Figure 3A:
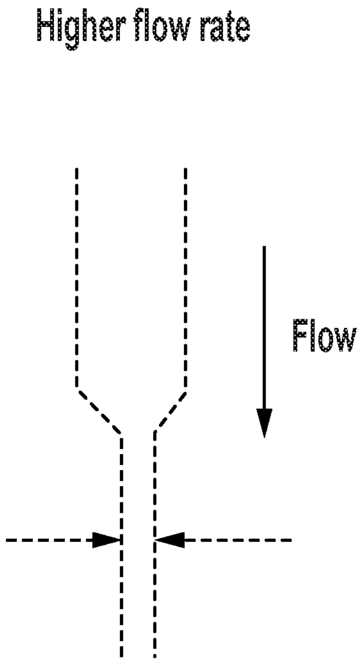
FIGS. 3A and 3B are schematics that depict the influence of diameter on the flow of liquid through the process conduits.
Figure 3B:
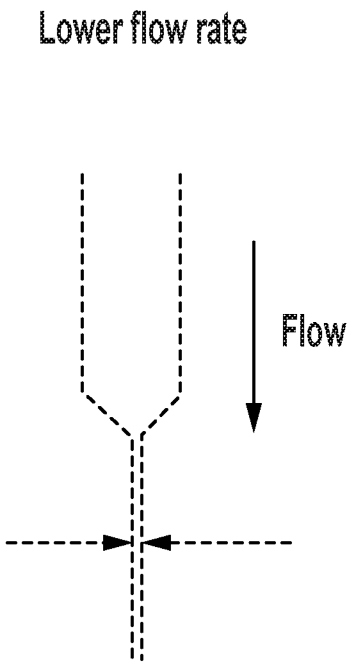
Figure 4A:
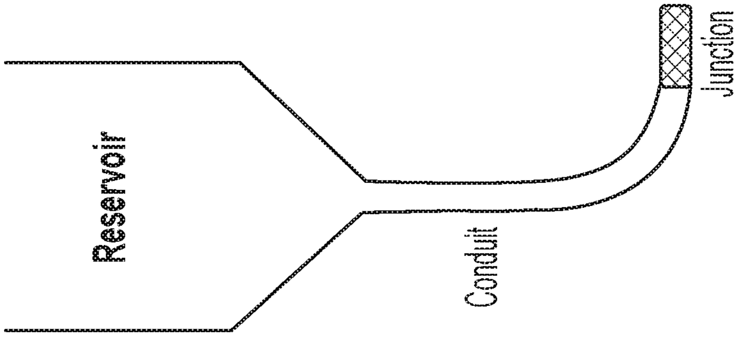
FIG. 4 (panels A-D) is a series of schematics that show exemplary locations to place constrictions to regulate the diameter and flow of liquid in the process.
Figure 4B:
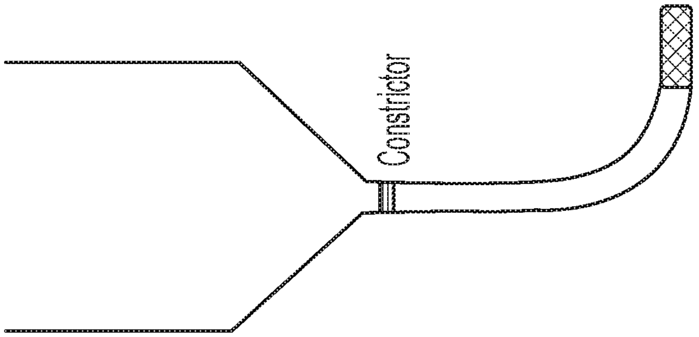
Figure 4C:
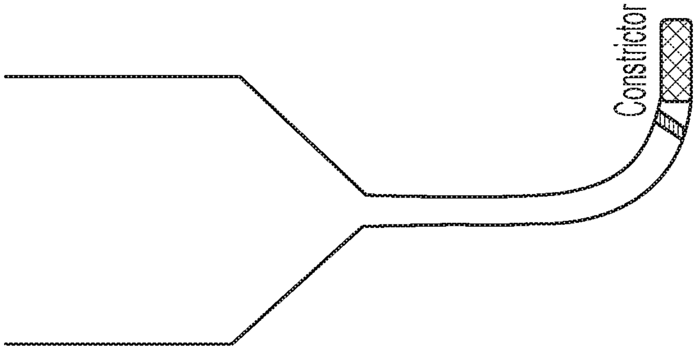
Figure 4D:
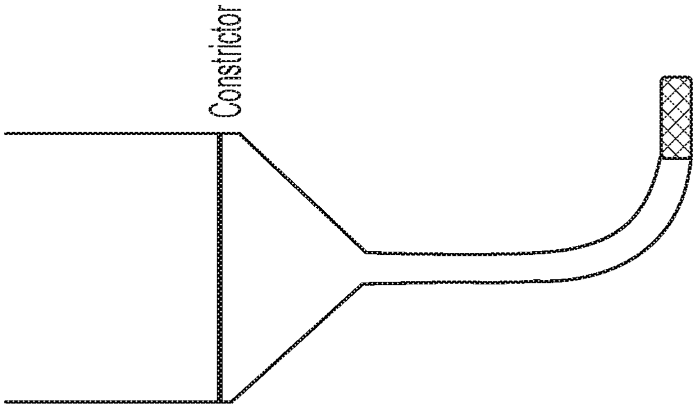

The liquid flow rate can be controlled in the process shown in FIG. 1 in order to achieve a desired flow rate and resultant mixing properties. One way to control the flow rates and the mixing of the solutions contained in the reservoirs is to adjust the diameter of at least one of the Reservoir (e.g. Reservoir 1 and/or Reservoir 2), the conduit, and/or the junction. FIGS. 3A and 3B illustrate adjustments to the diameter of a conduit and the resultant impact had on the liquid flow rate due to conduit diameter. As can be seen in FIGS. 3A and 3B, the larger the diameter, the greater the flow of liquid through the conduit.

One manner to achieve a desired diameter and resultant flow rate is by placing a constrictor (e.g., pinch bulb, lid, and clip) in one or more of the reservoir, conduit and/or junction. Placement of constrictors at each of these parts of the process is illustrated in FIG. 4A-4D. The placement of the constrictor will alter the diameter through which liquid flows from the reservoir, thus leading to adjustments in the flow rate and the mixing that occurs at the junction.

Figure 5A:
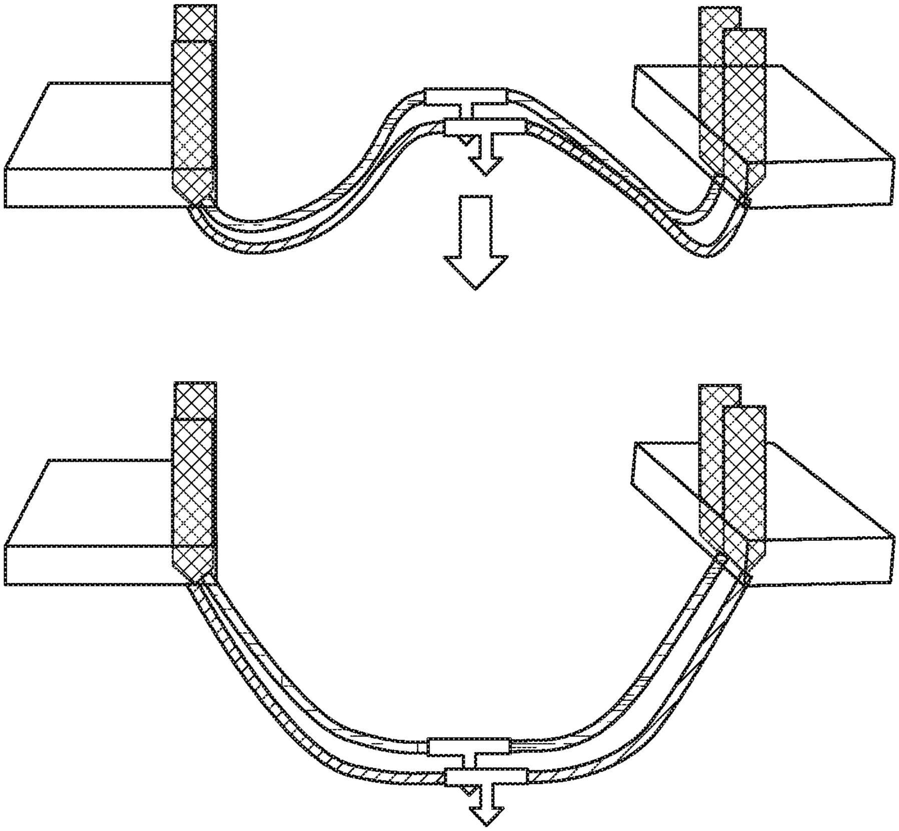
FIGS. 5A and 5B is a series of schematics that depict one embodiment used to control the flow rate and the resultant mixing in the process.
Figure 5B:
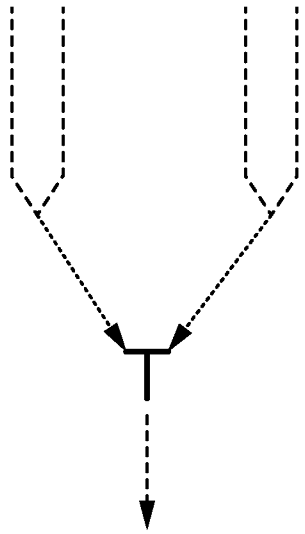
Figure 6:
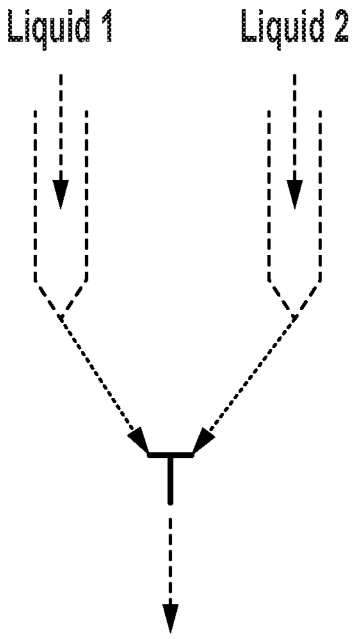
FIG. 6 depicts a schematic of the process in fixed system in which liquids in reservoirs 1 and 2 follow the flow of gravity, through the conduit, and mix at the junction.

Another manner to control the flow rate and the resultant mixing process is to move the connector upwards, such that the conduit lines are allowed to purge-fill, and at the same time restricting liquid flow due to height (i.e. gravity control). The liquids from Reservoir 1 and Reservoir 2 will mix upon moving the connector downwards. This manner of controlling the mixing process is illustrated in FIGS. 5A and 5B. Alternatively, the system can be held constant, adding liquids so that the formulation mix is the result of the fixed system. This is shown in FIG. 6.

Example 3: High Throughput Formulations Processes

The process as described herein can also be used in high-throughput scenarios. For example, a series of processes as described herein can be connected such that the process would comprise at least 10, 20, 30, 40, 50, 100, 150, 200, 250, 300 or more pairs of first conduit streams and second conduit streams. This would allow, for example, that the first conduit stream provide multiple mRNA solutions if so desired. Likewise, this the second conduit stream can provide multiple lipid solutions if so desired. In this manner, an assembly-line like approach is achieved, such that liquids are added to pairs of reservoirs at the same time, then the liquids are added to the next pairs of reservoirs in succession. This is illustrated in FIG. 7. An exemplary high throughput process is shown in FIG. 8.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A process of encapsulating messenger RNA (mRNA) in liposomes comprising:

a. providing a first stream comprising an mRNA solution at a first controlled flow rate from a first reservoir through a first conduit, b. providing a second stream comprising a lipid solution at a second controlled flow rate from a second reservoir through a second conduit, and c. mixing the first stream and the second stream at a junction comprising a T connector or a Y connector to form mRNA-encapsulated liposomes, wherein the first controlled flow rate, the second controlled flow rate, and the mixing are achieved using gravity and atmospheric pressure without use of a pump, and wherein the process results in an encapsulation efficiency of at least 75%.

2. The process of claim 1, wherein a first constriction controls the first controlled flow rate and a second constriction controls the second controlled flow rate.

3. The process of claim 2, wherein the first constriction and second constriction provide controlled flow rates that are the same.

4. The process of claim 2, wherein the first constriction and the second constriction provide controlled flow rates that are different.

5. The process of claim 4, wherein the first controlled flow rate to second controlled flow rate is at a ratio of about 1.2×, 1.5×, 1.8×, 2.0×, 2.5×, by 1.2× or greater, 1.5× or greater, 1.8× or greater, 2.0× or greater, or 2.5× or greater.

6. The process of claim 4, wherein the second controlled flow rate to first controlled flow rate is at a ratio of about 1.2×, 1.5×, 1.8×, 2.0×, 2.5×, by 1.2× or greater, 1.5× or greater, 1.8× or greater, 2.0× or greater, or 2.5× or greater.

7. The process of claim 2, wherein the first constriction comprises a first diameter of the first conduit and the second constriction comprises a second diameter of the second conduit.

8. The process of claim 7, wherein the first diameter of the first conduit is selected from the following ranges: 0.1 mm-1 mm, 1 mm-100 mm, 100 mm-1 cm, or 1 cm-100 cm.

9. The process of claim 7, wherein the second diameter of the second conduit is selected from the following ranges: 0.1 mm-1 mm, 1 mm-100 mm, 100 mm-1 cm, or 1 cm-100 cm.

10. The process of claim 2, wherein the first controlled flow rate ranges from about 0.1-1 mL/min, 1-150 mL/min, 150-250 mL/min, 250-500 mL/min, 500-1000 mL/min, 1000-2000 mL/min, 2000-3000 mL/min, 3000-4000 mL/min, or 4000-5000 mL/min.

11. The process of claim 2, wherein the second controlled flow rate ranges from about 0.1-1 mL/min, 1-150 mL/min, 150-250 mL/min, 250-500 mL/min, 500-1000 mL/min, 1000-2000 mL/min, 2000-3000 mL/min, 3000-4000 mL/min, or 4000-5000 mL/min.

* * * * *